United States Patent
Labit et al.

(10) Patent No.: US 8,430,857 B2
(45) Date of Patent: Apr. 30, 2013

(54) REUSABLE DIAPERS

(76) Inventors: Jennifer Lynn Labit, Arnold, MO (US);
James Andrew Labit, Arnold, MO (US)

( * ) Notice: Subject to any disclaimer, the term of this patent is extended or adjusted under 35 U.S.C. 154(b) by 0 days.

(21) Appl. No.: 13/351,733

(22) Filed: Jan. 17, 2012

(65) Prior Publication Data

US 2012/0116339 A1 May 10, 2012

Related U.S. Application Data

(63) Continuation of application No. 13/228,994, filed on Sep. 9, 2011, which is a continuation-in-part of application No. 12/059,844, filed on Mar. 31, 2008, now Pat. No. 8,062,276, which is a continuation-in-part of application No. 11/518,587, filed on Sep. 8, 2006, now Pat. No. 7,629,501.

(51) Int. Cl.
*A61F 13/15* (2006.01)
*A61F 13/20* (2006.01)

(52) U.S. Cl.
USPC .................. 604/385.11; 604/387

(58) Field of Classification Search ............ 604/385.01, 604/385.11, 378, 385.03, 385.14, 386–387
See application file for complete search history.

(56) References Cited

U.S. PATENT DOCUMENTS

| | | |
|---|---|---|
| 1,003,399 A | 9/1911 | Burns |
| 1,961,515 A | 6/1934 | Friedman |
| 2,016,355 A | 10/1935 | Alsop |
| 2,049,913 A | 8/1936 | Lesueur |
| RE20,315 E | 3/1937 | Lesueur |
| 2,292,030 A * | 8/1942 | Kraft .............................. 604/399 |
| 2,450,059 A | 9/1948 | Rickerson |
| 2,468,445 A | 4/1949 | Hurst |

(Continued)

FOREIGN PATENT DOCUMENTS

| | | |
|---|---|---|
| AU | 5039493 | 1/1994 |
| AU | 9539089 | 6/1996 |

(Continued)

OTHER PUBLICATIONS

Biodegradable Diapers, Real user reviews of Biodegradable Diapers, diapers that are good for babies, parents and the planet, CuteyBaby "One and Done!" Modern Cloth Diaper Starter Kit—GIRL, 5 pages, (Customer Review, Mar. 22, 2011) biodegradablediapers.info.

(Continued)

*Primary Examiner* — Michele M Kidwell
(74) *Attorney, Agent, or Firm* — Harness, Dickey & Pierce, P.L.C.

(57) ABSTRACT

A reusable diaper includes forward and rearward waist portions. At least one corner tab may be releasably attachable to the forward and rearward waist portions. The diaper may include at least one pocket configured to receive therein at least a portion of the corner tab. The pocket may be substantially impervious to liquids, such that positioning of the portion of the corner tab in the pocket helps inhibit wicking of liquid through the pocket and into the corner tab. Some embodiments may include first and second sets of interchangeable corner tabs that are releasably attachable to the forward and rearward waist portions. The second set of corner tabs may be sized differently than the first set of corner tabs such that the diaper size is adjustable depending on whether the first or second set of corner tabs are used.

22 Claims, 23 Drawing Sheets

U.S. PATENT DOCUMENTS

| | | | |
|---|---|---|---|
| 2,493,492 A | 1/1950 | Malamut | |
| 2,523,079 A | 9/1950 | Walter et al. | |
| 2,532,029 A | 11/1950 | Medoff | |
| 2,545,216 A | 3/1951 | Toussie | |
| 2,568,590 A | 9/1951 | Laser | |
| 2,575,164 A | 11/1951 | Donovan | |
| 2,577,398 A | 12/1951 | Blake | |
| 2,581,904 A | 1/1952 | Burns | |
| 2,591,079 A | 4/1952 | Leaton | |
| 2,605,558 A | 8/1952 | Kennette | |
| 2,607,348 A | 8/1952 | Rosenblatt | |
| 2,627,859 A | 2/1953 | Hargrave | |
| 2,664,895 A | 1/1954 | Shulman | |
| 2,688,328 A | 9/1954 | Marcus | |
| 2,703,577 A * | 3/1955 | May | 604/399 |
| 2,733,715 A * | 2/1956 | Folk | 604/398 |
| 2,788,786 A | 4/1957 | Dexter | |
| 2,826,199 A | 3/1958 | Brandon | |
| 2,853,073 A | 9/1958 | Brafman | |
| 2,866,459 A | 12/1958 | Sobelson | |
| 2,868,205 A | 1/1959 | Epstein | |
| 2,893,393 A | 7/1959 | Pressley | |
| 2,910,982 A | 11/1959 | Woodward | |
| 2,985,170 A | 5/1961 | Title | |
| 3,049,124 A * | 8/1962 | Thompson | 604/399 |
| 3,141,461 A | 7/1964 | Farris | |
| 3,162,196 A | 12/1964 | Salk | |
| 3,341,394 A | 9/1967 | Kinney | |
| 3,485,706 A | 12/1969 | Evans | |
| 3,530,859 A | 9/1970 | Helmowitz | |
| 3,559,648 A | 2/1971 | Mason, Jr. | |
| 3,658,064 A | 4/1972 | Pociluyko | |
| 3,667,466 A | 6/1972 | Ralph | |
| 3,741,212 A | 6/1973 | Schutte | |
| 3,769,978 A | 11/1973 | DeNight et al. | |
| 3,882,871 A | 5/1975 | Taniguchi | |
| RE28,483 E | 7/1975 | Ralph | |
| 3,926,189 A | 12/1975 | Taylor | |
| 4,037,602 A | 7/1977 | Hawthorne | |
| 4,338,939 A | 7/1982 | Daville | |
| D269,907 S | 7/1983 | Tong | |
| 4,414,971 A | 11/1983 | Chung et al. | |
| 4,548,604 A | 10/1985 | Ellsworth | |
| 4,568,342 A * | 2/1986 | Davis | 604/391 |
| 4,573,987 A | 3/1986 | Lamb, Jr. | |
| 4,643,726 A | 2/1987 | Gegelys | |
| 4,671,793 A | 6/1987 | Hults et al. | |
| 4,681,581 A | 7/1987 | Coates | |
| 4,695,279 A | 9/1987 | Steer | |
| 4,704,117 A | 11/1987 | Mitchell | |
| 4,773,906 A * | 9/1988 | Krushel | 604/391 |
| 4,834,737 A | 5/1989 | Khan | |
| 4,850,987 A | 7/1989 | Gilomen et al. | |
| 4,892,598 A | 1/1990 | Stevens et al. | |
| 4,904,251 A | 2/1990 | Igaue et al. | |
| 4,906,243 A | 3/1990 | Dravland | |
| 4,928,323 A | 5/1990 | Nathan | |
| 4,950,263 A | 8/1990 | Lewis | |
| 4,961,736 A | 10/1990 | McCloud | |
| 4,978,345 A | 12/1990 | Holiday et al. | |
| 4,981,480 A * | 1/1991 | Gaudet et al. | 604/386 |
| 5,019,068 A | 5/1991 | Perez et al. | |
| 5,069,672 A | 12/1991 | Wippler et al. | |
| 5,100,399 A * | 3/1992 | Janson et al. | 604/386 |
| 5,106,382 A | 4/1992 | Henry | |
| 5,108,385 A | 4/1992 | Snyder | |
| 5,135,522 A | 8/1992 | Fahrenkrug et al. | |
| 5,137,526 A | 8/1992 | Coates | |
| 5,185,011 A | 2/1993 | Strasser | |
| 5,188,626 A | 2/1993 | Toyoda et al. | |
| 5,207,662 A | 5/1993 | James | |
| 5,217,447 A | 6/1993 | Gagnon | |
| D339,633 S | 9/1993 | Porter | |
| 5,306,267 A | 4/1994 | Hahn et al. | |
| 5,325,543 A | 7/1994 | Allen | |
| 5,342,340 A | 8/1994 | Kichefski et al. | |
| 5,360,422 A | 11/1994 | Brownlee et al. | |
| D354,809 S | 1/1995 | Eskey | |
| 5,399,177 A | 3/1995 | Blaney et al. | |
| 5,405,342 A | 4/1995 | Roessler et al. | |
| 5,409,476 A | 4/1995 | Coates | |
| D362,717 S | 9/1995 | Caschette et al. | |
| 5,454,799 A | 10/1995 | Lakiss-Smith et al. | |
| 5,458,591 A | 10/1995 | Roessler et al. | |
| 5,476,457 A | 12/1995 | Roessler et al. | |
| D366,112 S | 1/1996 | Tollin et al. | |
| 5,514,121 A | 5/1996 | Roe et al. | |
| 5,527,300 A | 6/1996 | Sauer | |
| 5,611,789 A | 3/1997 | Seth | |
| 5,613,959 A | 3/1997 | Roessler et al. | |
| D386,582 S | 11/1997 | Levine | |
| 5,695,488 A | 12/1997 | Sosalla | |
| 5,706,524 A | 1/1998 | Herrin et al. | |
| 5,722,127 A | 3/1998 | Coates | |
| 5,725,518 A | 3/1998 | Coates | |
| 5,814,037 A | 9/1998 | Coates | |
| 5,853,403 A | 12/1998 | Tanzer et al. | |
| 5,891,122 A | 4/1999 | Coates | |
| D436,400 S | 1/2001 | Kiecker | |
| 6,168,583 B1 | 1/2001 | Tanji et al. | |
| 6,193,702 B1 | 2/2001 | Spencer | |
| 6,254,583 B1 | 7/2001 | Coates | |
| 6,315,764 B1 | 11/2001 | Faulks et al. | |
| 6,322,552 B1 | 11/2001 | Blenke et al. | |
| 6,379,343 B2 | 4/2002 | Stephenson et al. | |
| 6,383,170 B1 | 5/2002 | Mishima et al. | |
| 6,402,731 B1 | 6/2002 | Surprise et al. | |
| 6,423,047 B1 | 7/2002 | Webster | |
| 6,471,681 B1 | 10/2002 | Ronnberg et al. | |
| 6,482,194 B1 | 11/2002 | Putzer | |
| 6,540,730 B1 | 4/2003 | Niedermeyer | |
| 6,562,016 B2 | 5/2003 | Shinkai | |
| 6,569,137 B2 | 5/2003 | Suzuki et al. | |
| 6,579,273 B2 * | 6/2003 | Dupuy | 604/385.14 |
| 6,616,645 B1 | 9/2003 | Moravek | |
| 6,623,466 B1 | 9/2003 | Richardson | |
| 6,641,569 B1 | 11/2003 | Coles et al. | |
| 6,766,817 B2 | 7/2004 | da Silva et al. | |
| 6,767,498 B1 | 7/2004 | Talley et al. | |
| 6,918,404 B2 | 7/2005 | Dias da Silva et al. | |
| 6,932,800 B2 | 8/2005 | LaVon et al. | |
| 6,989,005 B1 | 1/2006 | LaVon et al. | |
| 7,066,586 B2 | 6/2006 | da Silva et al. | |
| 7,244,398 B2 | 7/2007 | Kotary et al. | |
| 7,264,615 B2 | 9/2007 | Sherrod et al. | |
| 7,285,255 B2 | 10/2007 | Kadlec et al. | |
| 7,361,803 B2 | 4/2008 | Miskie | |
| 7,591,811 B2 | 9/2009 | Crislip Wilkinson | |
| 7,629,501 B2 | 12/2009 | Labit et al. | |
| 7,914,507 B1 * | 3/2011 | Magee | 604/385.01 |
| 2002/0010452 A1 * | 1/2002 | Dupuy | 604/385.14 |
| 2002/0094740 A1 | 7/2002 | Li et al. | |
| 2002/0111596 A1 * | 8/2002 | Fletcher et al. | 604/385.03 |
| 2003/0014024 A1 | 1/2003 | Kiecker | |
| 2003/0083635 A1 | 5/2003 | Gibbs | |
| 2003/0109841 A1 | 6/2003 | Edwards | |
| 2004/0044323 A1 | 3/2004 | Roessler et al. | |
| 2004/0082933 A1 | 4/2004 | Karami | |
| 2004/0236298 A1 | 11/2004 | Coates | |
| 2004/0236300 A1 | 11/2004 | Gibbs et al. | |
| 2004/0267219 A1 | 12/2004 | Olmedo | |
| 2005/0085784 A1 | 4/2005 | LeMinh et al. | |
| 2005/0148258 A1 | 7/2005 | Chakravarty et al. | |
| 2005/0210560 A1 | 9/2005 | Coates | |
| 2005/0228356 A1 | 10/2005 | LaVon et al. | |
| 2006/0167432 A1 | 7/2006 | Sigari | |
| 2007/0066952 A1 | 3/2007 | LaVon et al. | |
| 2008/0015531 A1 | 1/2008 | Hird et al. | |
| 2008/0065039 A1 | 3/2008 | Labit et al. | |
| 2008/0183148 A1 | 7/2008 | Labit et al. | |
| 2008/0195075 A1 * | 8/2008 | Ruocco | 604/385.15 |
| 2009/0216209 A1 * | 8/2009 | Ekstrom | 604/367 |
| 2010/0036340 A1 | 2/2010 | Allison-Rogers | |
| 2010/0087794 A1 | 4/2010 | Labit et al. | |
| 2010/0108554 A1 | 5/2010 | Melius et al. | |
| 2010/0130955 A1 | 5/2010 | Tice | |
| 2010/0318057 A1 * | 12/2010 | Yakem | 604/396 |

| | | | |
|---|---|---|---|
| 2011/0137278 A1 | 6/2011 | Ormsby et al. | |
| 2011/0202030 A1 | 8/2011 | Ronström | |
| 2011/0301561 A1* | 12/2011 | Tournier | 604/377 |
| 2011/0319852 A1 | 12/2011 | Labit | |
| 2012/0172827 A1 | 7/2012 | Dupuy | |

FOREIGN PATENT DOCUMENTS

| | | |
|---|---|---|
| BR | 03606/71 | 12/1971 |
| BR | 360571 | 12/1971 |
| CA | 2024375 | 3/1992 |
| CA | 2097437 | 12/1993 |
| CA | 2103537 A | 2/1995 |
| DE | 4326271 | 2/1995 |
| EP | 0099846 | 2/1984 |
| EP | 0486006 | 11/1991 |
| EP | 0475702 | 3/1992 |
| EP | 0605013 | 7/1994 |
| EP | 2106775 | 10/2009 |
| ES | 2115559 | 6/1998 |
| GB | 493819 | 10/1938 |
| GB | 0849573 | 9/1960 |
| GB | 08037160 | 2/2008 |
| JP | 04150853 | 5/1992 |
| JP | 08000662 | 1/1996 |
| WO | WO 87/05471 | 9/1987 |
| WO | WO 90/07313 | 7/1990 |
| WO | WO 94/03137 | 2/1994 |
| WO | WO 94/15563 | 7/1994 |
| WO | WO 95/23569 | 9/1995 |
| WO | 97/38656 | 10/1997 |
| WO | WO 98/24388 | 6/1998 |
| WO | WO 99/33421 | 7/1999 |
| WO | WO 2008/030984 | 3/2008 |
| WO | WO 2008/142634 | 11/2008 |
| WO | WO 2009/106899 | 9/2009 |
| WO | WO 2009/146021 | 12/2009 |
| ZA | 8701842 | 11/1988 |

OTHER PUBLICATIONS

Biodegradable Diapers, Real user reviews of Biodegradable Diapers, diapers that are good for babies, parents and the planet, CuteyBaby "One and Done!" Modern Cloth Diaper Starter Kit—GIRL, 5 pages, (Customer Review, Jun. 3, 2010) biodegradablediapers.info.
Biodegradable Diapers, Real user reviews of Biodegradable Diapers, diapers that are good for babies, parents and the planet, CuteyBaby "One and Done!" Modern Cloth Diaper Starter Kit—GIRL, 5 pages, (Customer Review, May 22, 2010) biodegradablediapers.info.
Derwent abstract and Figure of CA 2024375A, publication date Mar. 1, 1992.
FuzziBunz, A better diaper for a better planet, Newsletter, FuzziBunz Press Releases, 2 pages, (Jul. 10, 2007).
http://fuzzibunz.com/Fuzzi-Bunz-Colors.htm, 2 pages, accessed and printed Sep. 8, 2006.
http://getantsy.com/Antsy-Pants-Are.html, Antsy Pants™ Pull-Up Cloth Diapers, Optimized for Potty Training, 2009-2011, 6 pages, accessed and printed Sep. 21, 2011.
http://hydrology-tubarc.blogspot.com/32 pages, accessed Sep. 15, 2008.
http://ip-know-how-tubarc.blogspot.com/, 8 pages, accessed Sep. 15, 2008.
http://tubarc.blogspot.com/, 206 pages, accessed Sep. 15, 2008.
http://web.archive.org/web/20041010045134/www.changingbabies.com/anatomyof-adiaper.html, accessed Apr. 27, 2007, 17 pages.
http://www.cottonbabies.com/index.php, 7 pages, accessed on Aug. 24, 2006.
http://www.diapersite.com/baby_diapers_specs.htrn, 4 pages, accessed Apr. 23, 2008.
http://www.diapersite.com/images/diaperspecs/velcro.htm, 1 page, accessed Apr. 23, 2008.
http://www.gro-via.com/aiotutorial.html, 2011 The Natural Baby Company, 4 pages, accessed and printed Sep. 21, 2011.
http://www.tinytush.com/, 6 pages, accessed and printed Sep. 8, 2006.
http://www.wonderworksbabyco.com/products.htm, 5 pages, accessed and printed Sep. 8, 2006.
http:www.aplix.com/en/layout/set/print/content/search, accessed Apr. 27, 2007, 3 pages.
https://www.gro-via.com/mychoice-trainer.html, 2011 The Natural Baby Company, 5 pages, accessed and printed Sep. 21, 2011.
Definition of "Waterproof", Webster's Third New International Dictionary, unabridged, 1993, 1 page.
International Search Report and Written Opinion for PCT International Application No. PCT/US2012/053613 dated Jan. 29, 2012; 10 pgs.; which claims the same priority, U.S. Appl. No. 13/228,994, filed Sep. 9, 2011, as the instant application.

* cited by examiner

REUSABLE DIAPERS

CROSS-REFERENCE TO RELATED APPLICATIONS

This application is a continuation of U.S. patent application Ser. No. 13/228,994 filed Sep. 9, 2011, which is a continuation-in-part of U.S. patent application Ser. No. 12/059,844 filed Mar. 31, 2008 (published Sep. 4, 2008 as US 2008/0215027), which, in turn, is a continuation-in-part of U.S. patent application Ser. No. 11/518,587 filed Sep. 8, 2006 (now U.S. Pat. No. 7,629,501 issued Dec. 8, 2009). The entire disclosures of each of the above applications are incorporated herein by reference.

FIELD

The present disclosure relates generally to reusable diapers.

BACKGROUND

This section provides background information related to the present disclosure which is not necessarily prior art.

Absorbent articles, such as disposable diapers, training pants, or incontinence pads, generally have an absorbent core intended for single use only. Once the absorbent core component is saturated with bodily discharges, such as urine, the entire absorbent article is usually discarded. Oftentimes, parts of a disposable diaper or training pants could be reused. But with the unitary construction, they are nevertheless discarded along with the saturated absorbent cores. In addition to the added cost and waste associated with discarding such products, it is often inconvenient to acquire and store quantities of such disposable absorbent articles.

SUMMARY

This section provides a general summary of the disclosure, and is not a comprehensive disclosure of its full scope or all of its features.

According to various aspects, exemplary embodiments of reusable diapers are disclosed herein. In an exemplary embodiment, a reusable diaper generally includes forward and rearward waist portions. At least one corner tab is releasably attachable to the forward and rearward waist portions, such that the corner tab is detachable and completely separable from the diaper. There is at least one pocket substantially impervious to liquids, which is configured to receive therein at least a portion of the corner tab when the forward and rearward waist portions are releasably attached by the corner tab. The positioning of the portion of the corner tab in the pocket helps inhibit wicking of liquid through the pocket and into the corner tab.

In another exemplary embodiment, a reusable diaper generally includes forward and rearward waist portions. First and second sets of corner tabs are releasably attachable to the forward and rearward waist portions, such that the second set of corner tabs is interchangeable with the first set of corner tabs. The second set of corner tabs sized differently than the first set of corner tabs such that the diaper has a first size when the forward and rearward waist portions are releasably attached by the first set of corner tabs, and such that the diaper has a second size different than the first size when the forward and rearward waist portions are releasably attached by the second set of corner tabs.

In another exemplary embodiment, a reusable diaper generally includes forward and rearward waist portions. A first pocket is disposed in a lateral side portion of the forward waist portion. A second pocket is disposed in an opposite lateral side portion of the forward waist portion. A third pocket is disposed in a lateral side portion of the rearward waist portion. A fourth pocket is disposed in an opposite lateral side portion of the rearward waist portion. First and second pairs of corner tabs each have front and back end portions releasably attachable to the respective forward and rearward waist portions within the respective first, second, third, and fourth pockets, such that the second pair of corner tabs is interchangeable with the first pair of corner tabs. The second pair of corner tabs is sized differently than the first pair of corner tabs. The corner tabs define portions of the waist and leg openings of the diaper when releasably attached to the forward and rearward waist portions, such that interchanging the first and second pairs of corner tabs changes the size of the waist and leg openings of the diaper.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 13:
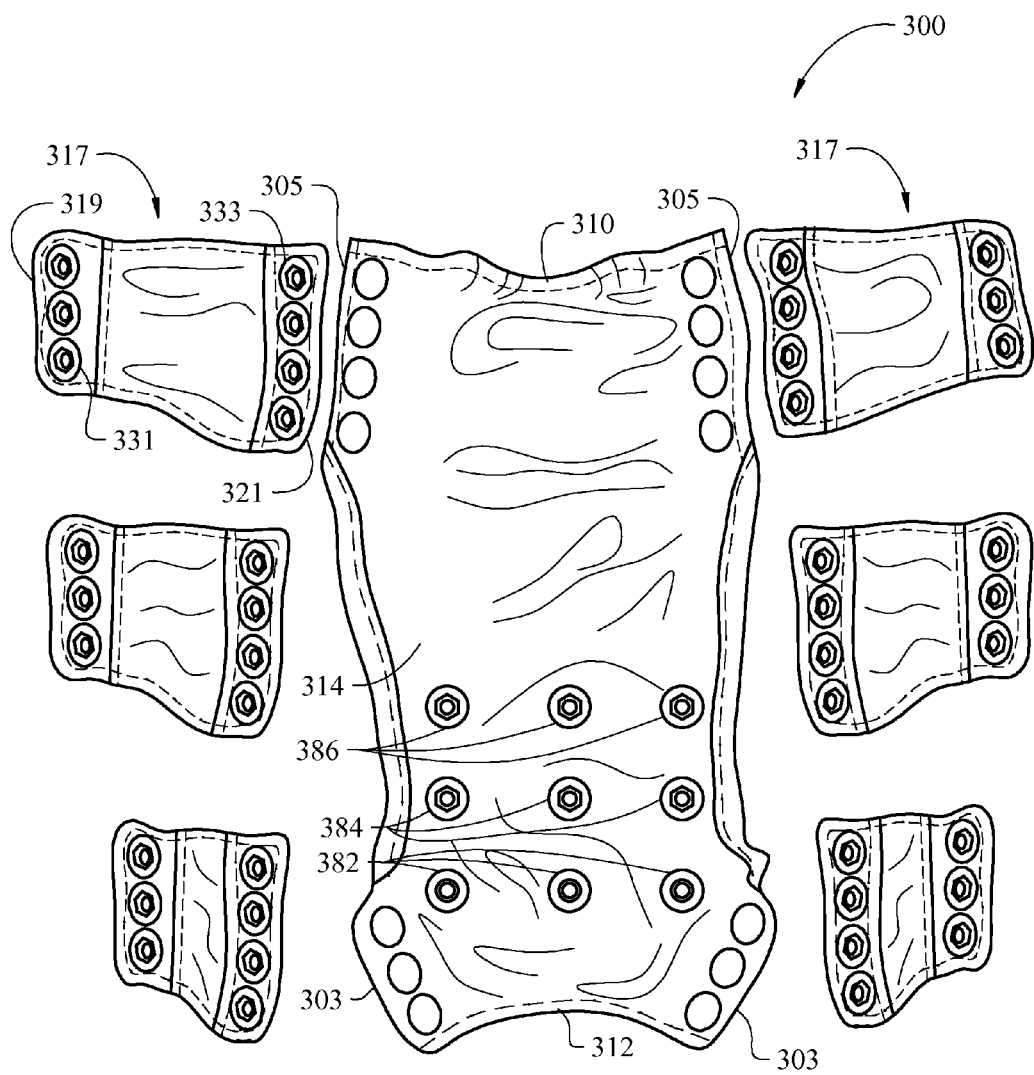
FIG. 13 is a perspective view of another exemplary embodiment of a reusable diaper, and illustrating interchangeable sets of corner tabs of different sizes that are releasably attachable to the reusable diaper for adjusting and tailoring the diaper size to the wearer.
Figure 14:
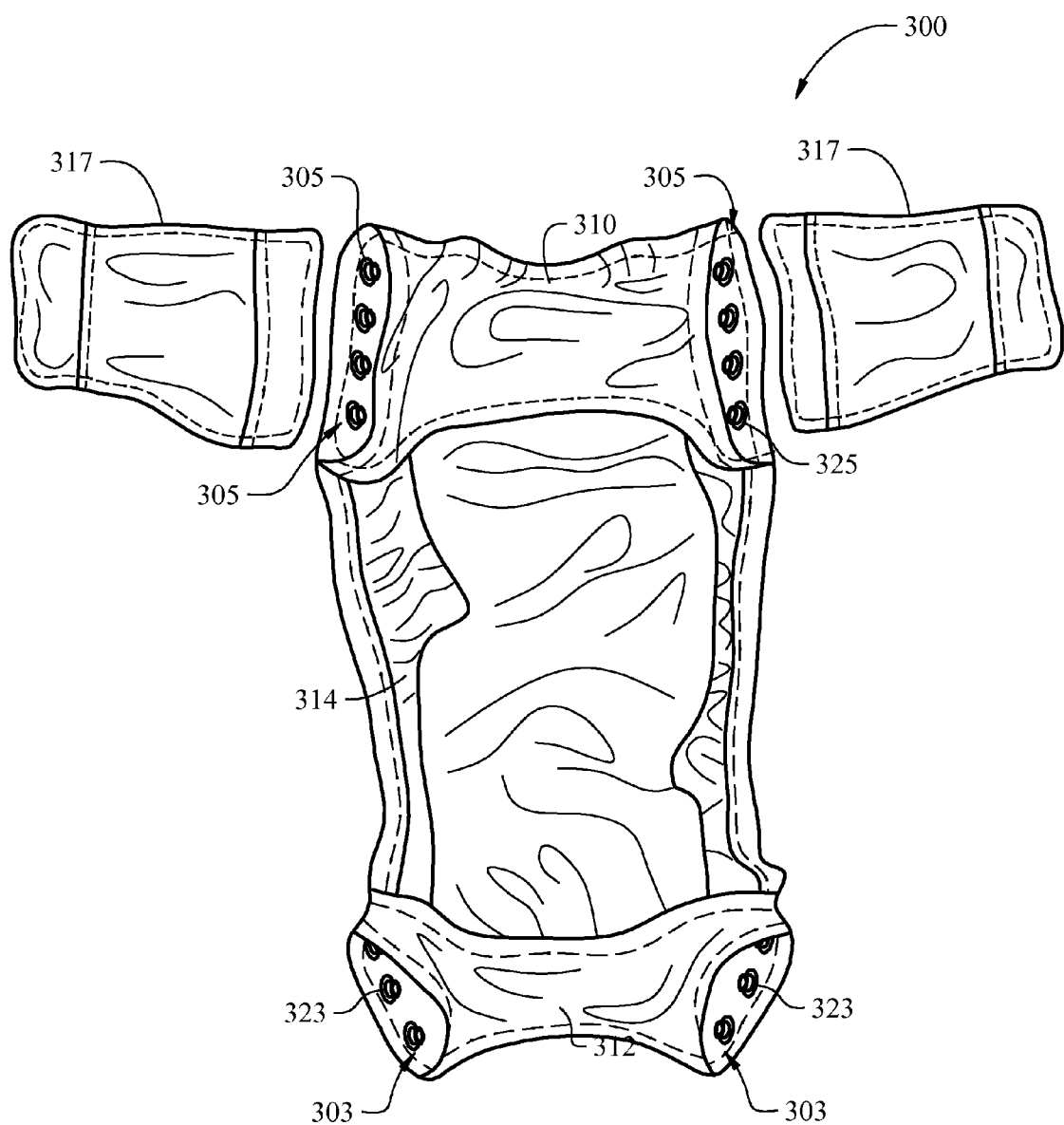
FIG. 14 is an inner view of the reusable diaper shown in FIG. 13 illustrating the pockets and snap members therein for releasably attaching the corner tabs to the reusable diaper.
Figure 15:
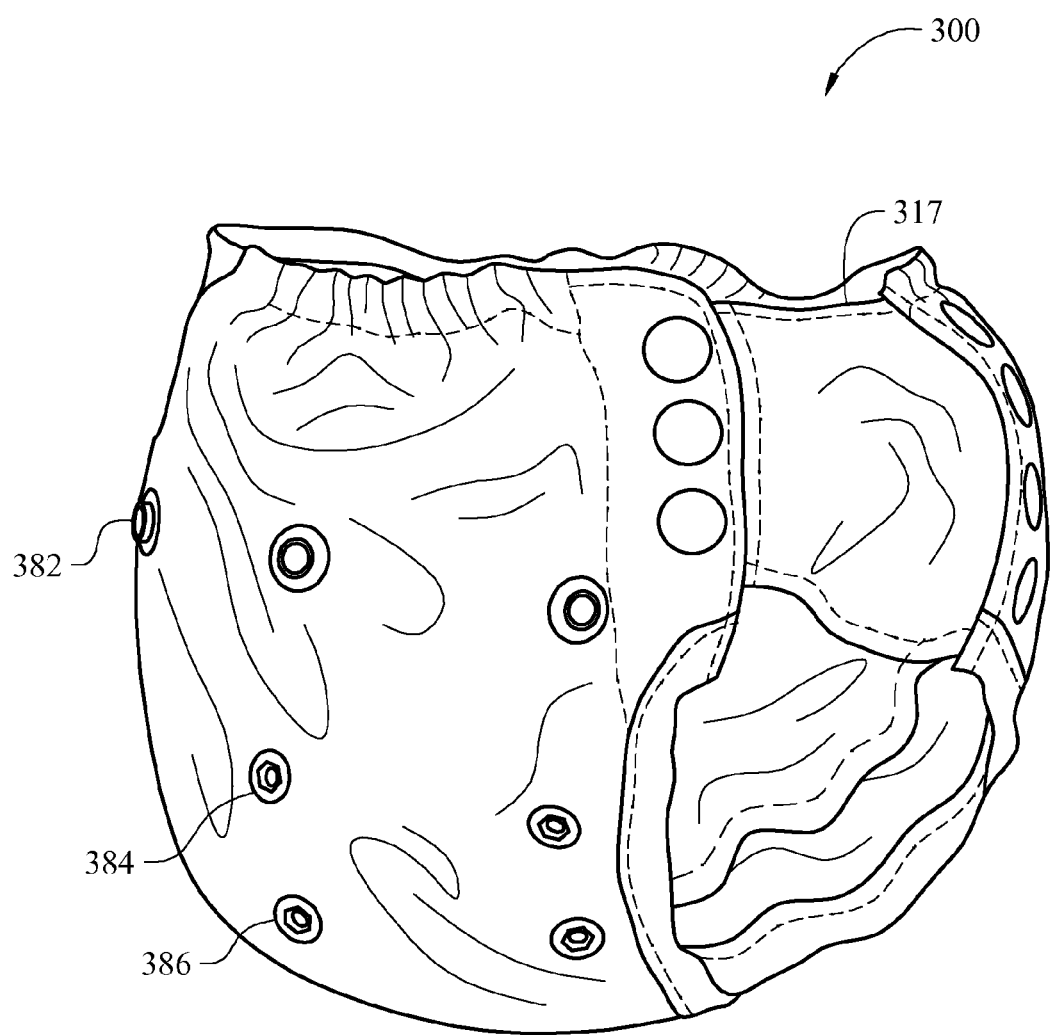
FIG. 15 is a perspective view of the reusable diaper shown in FIG. 13 wherein the longest corner tabs are releasably attached to the reusable diaper without any of the snap members along the diaper's forward portion snapped together.
Figure 16:
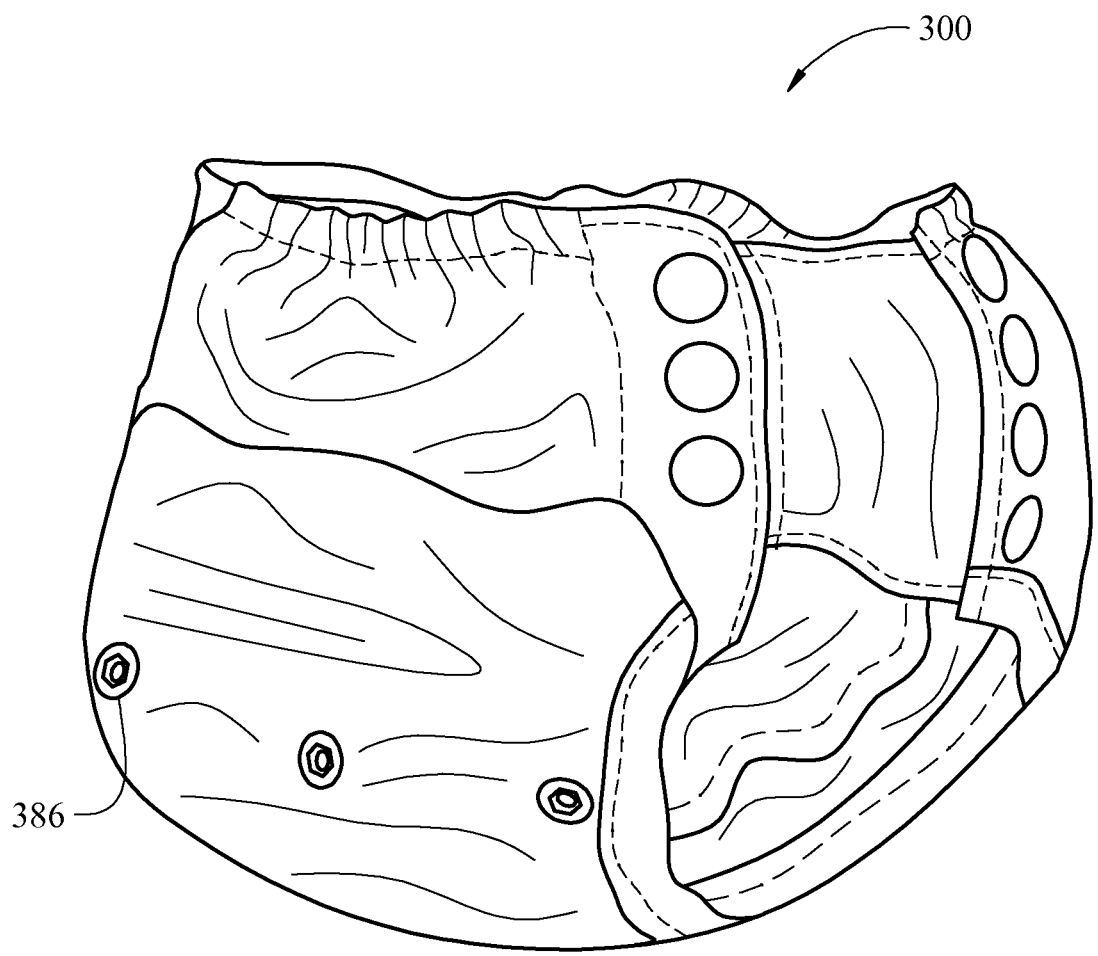
Figure 17:
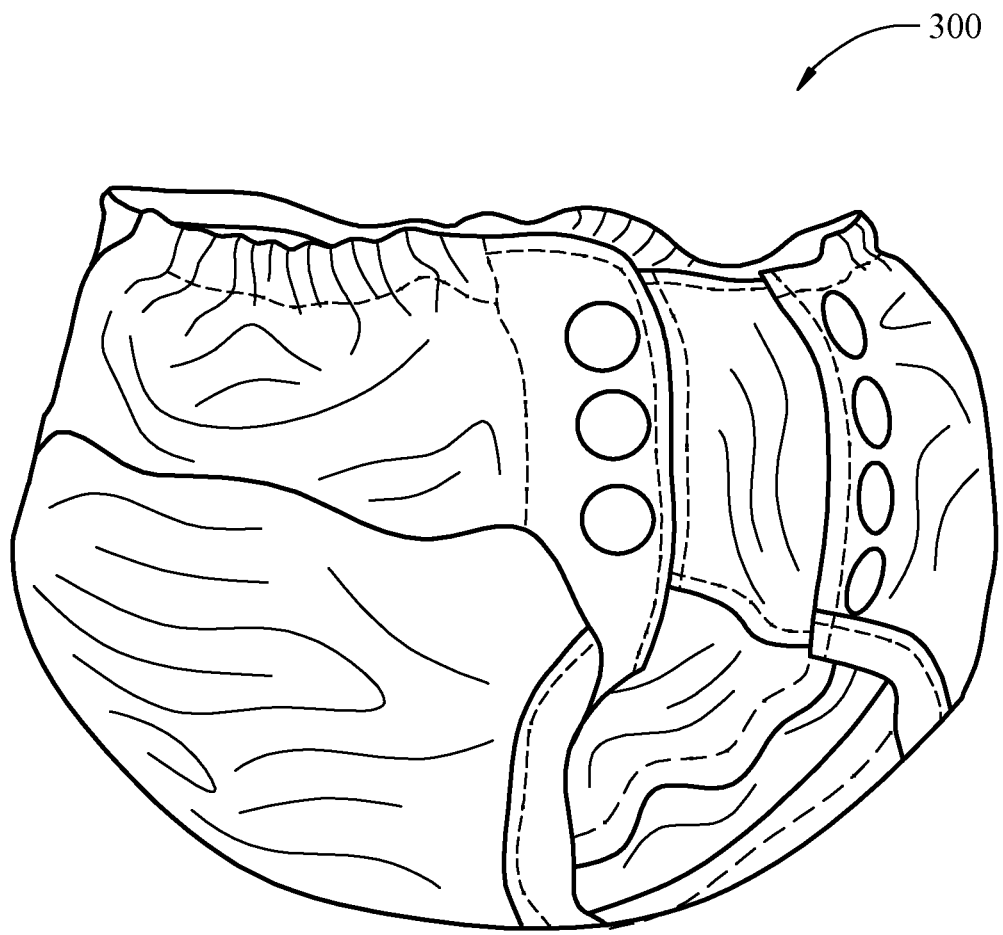
Figures 18A, 18B, 18C:
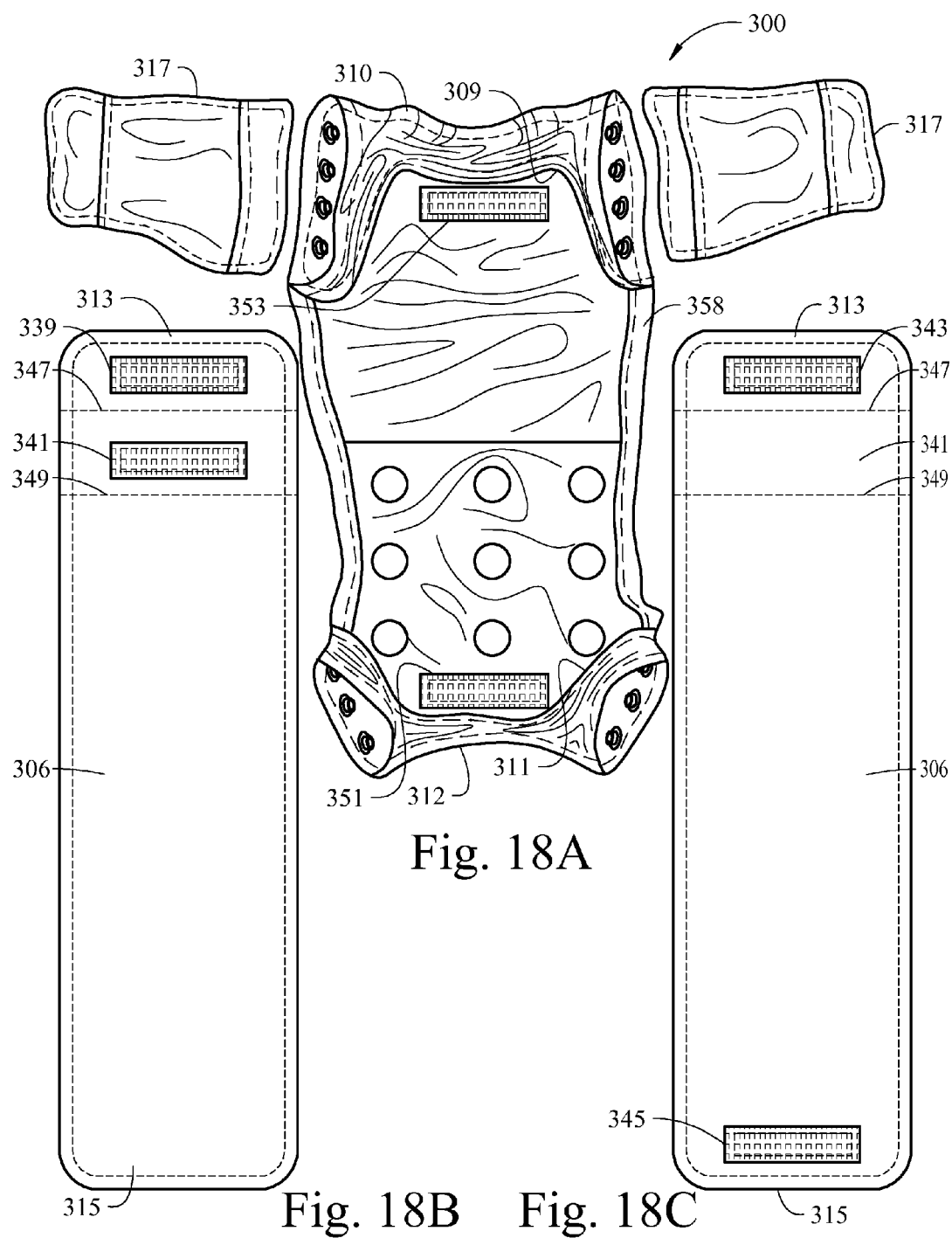
Figure 19:
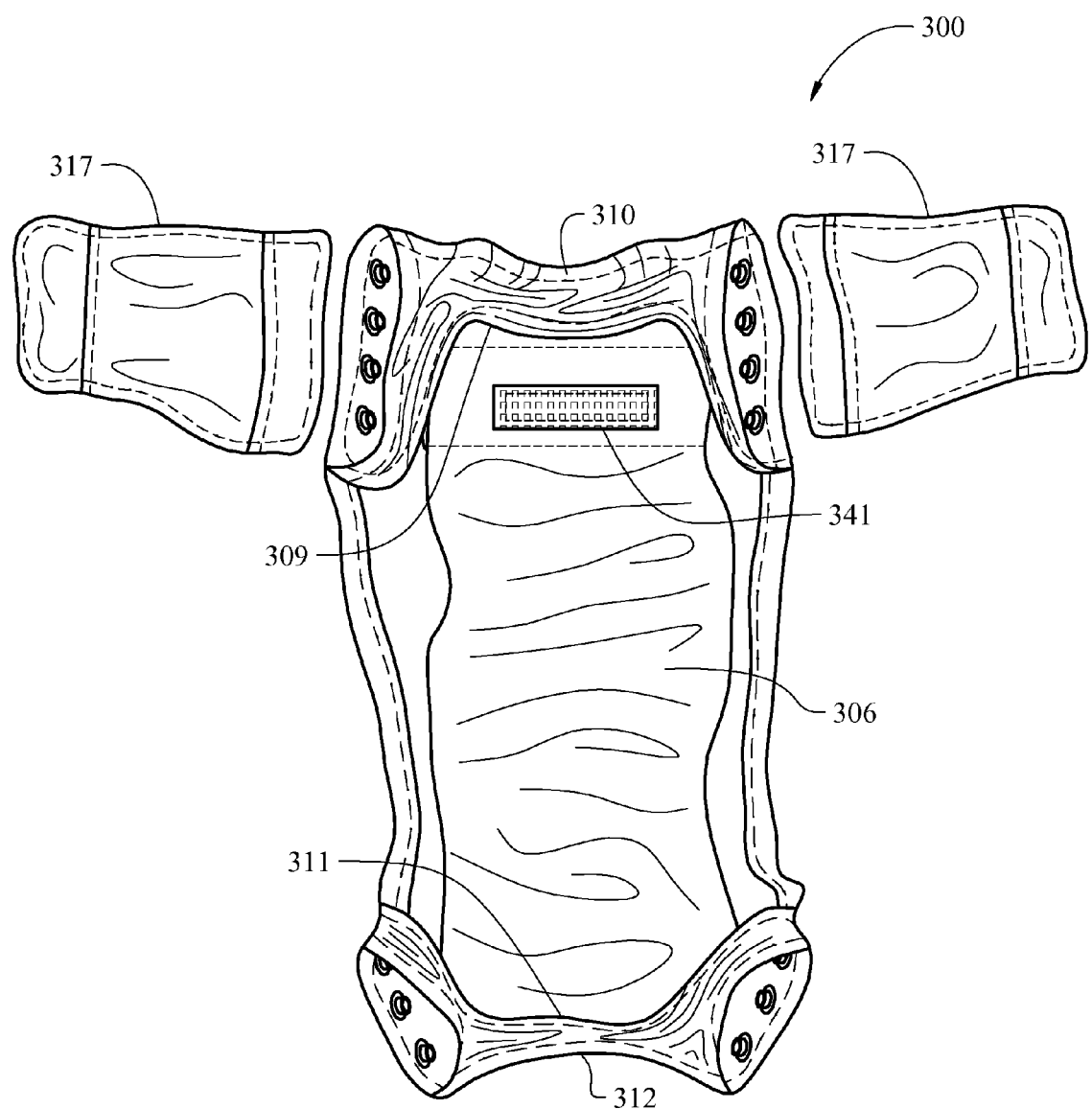
Figure 20:
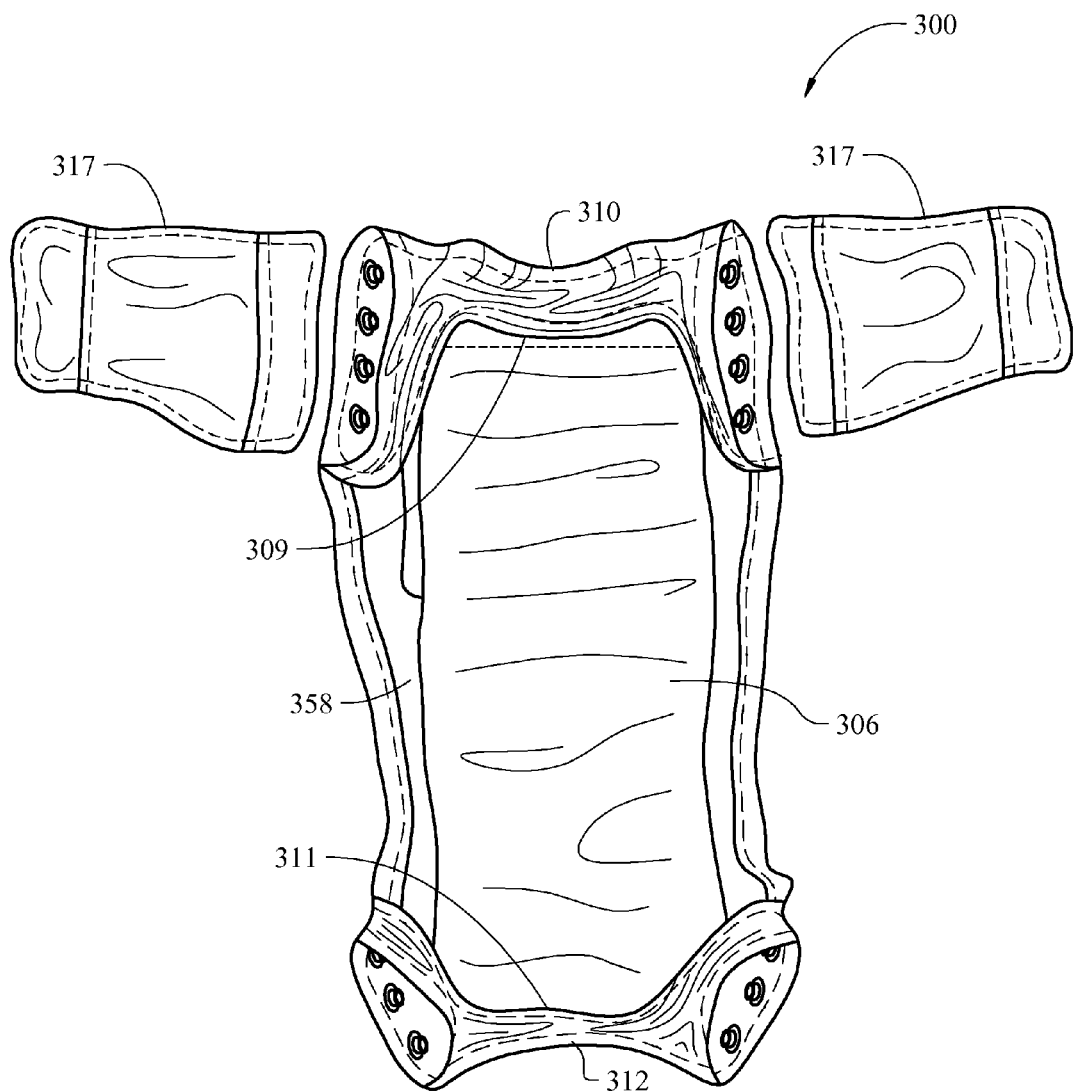
Figure 21:
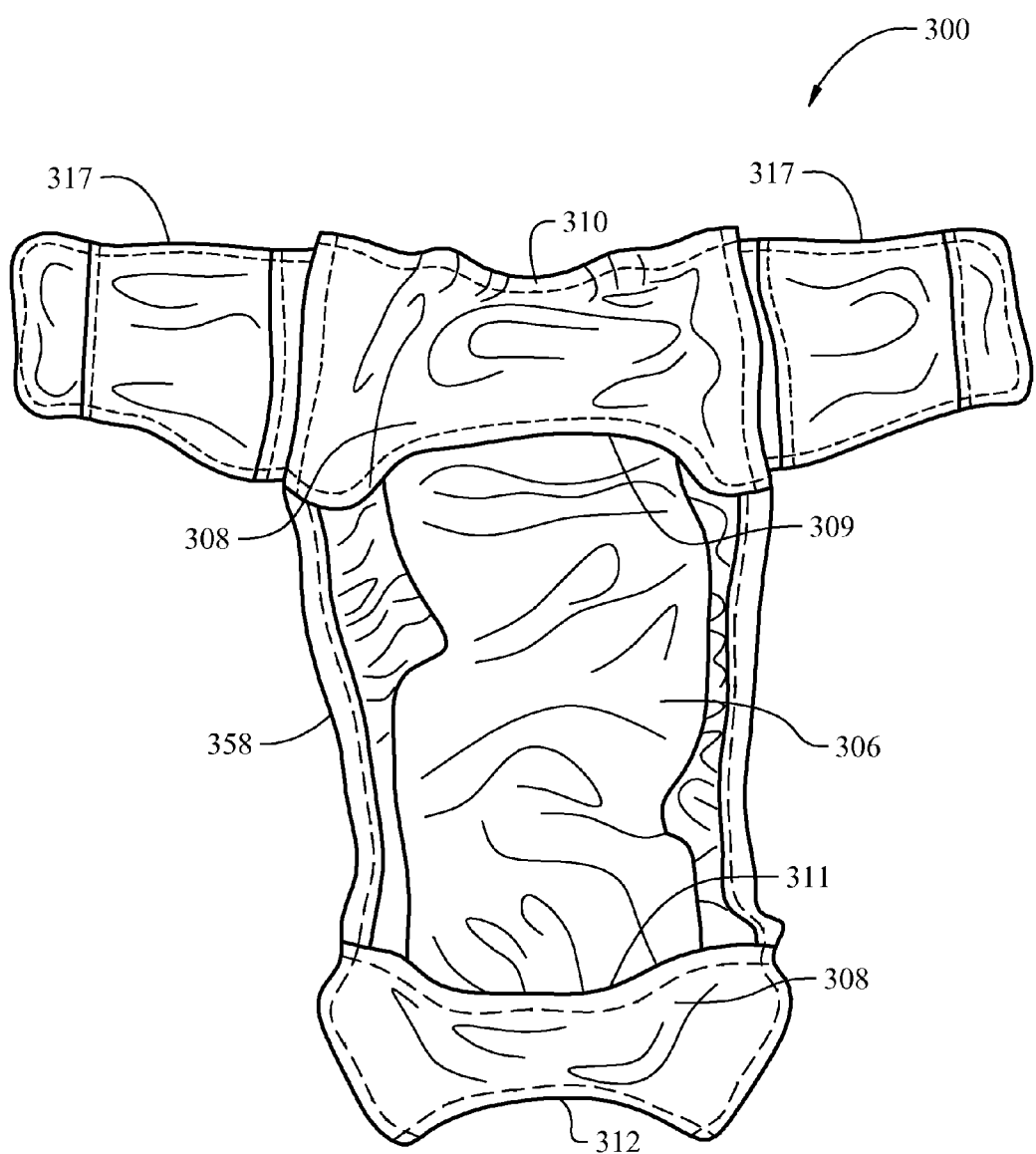
Figure 22:
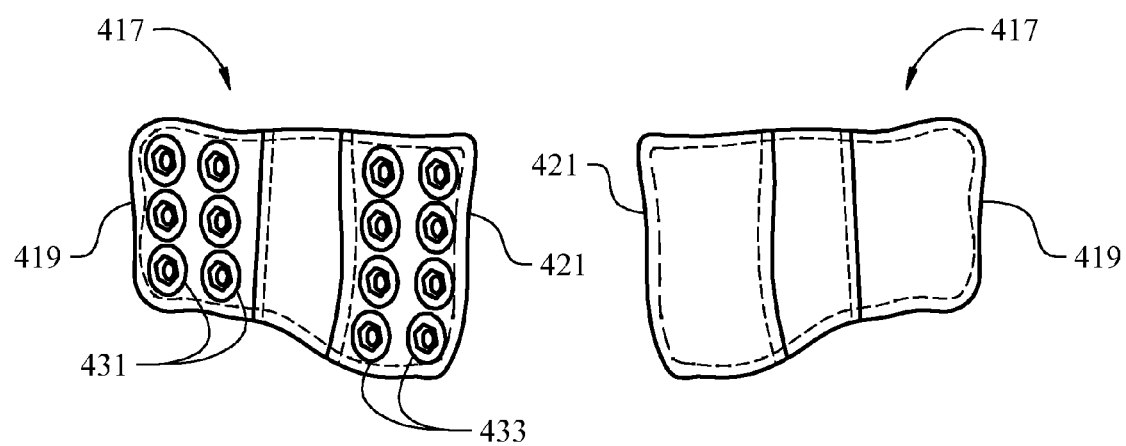
Figure 23:
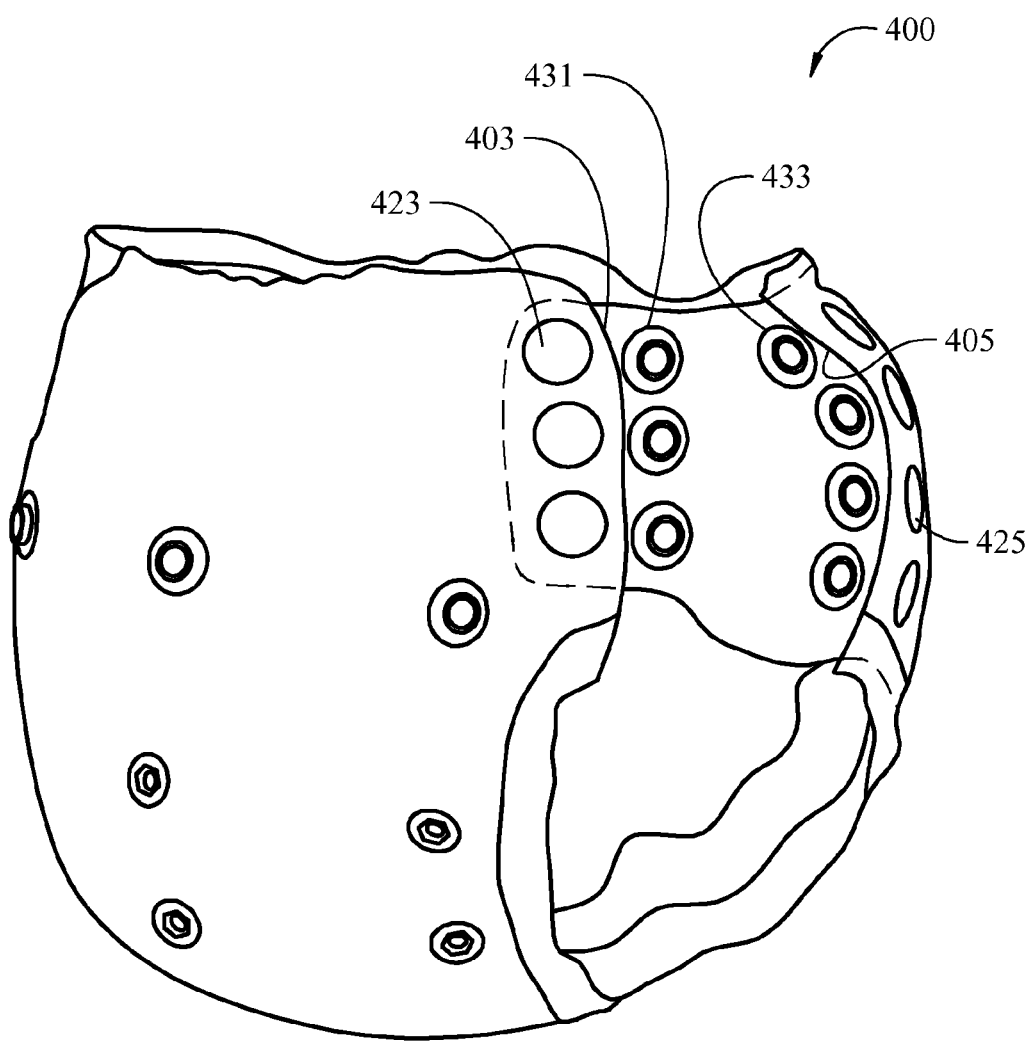
Figure 24:
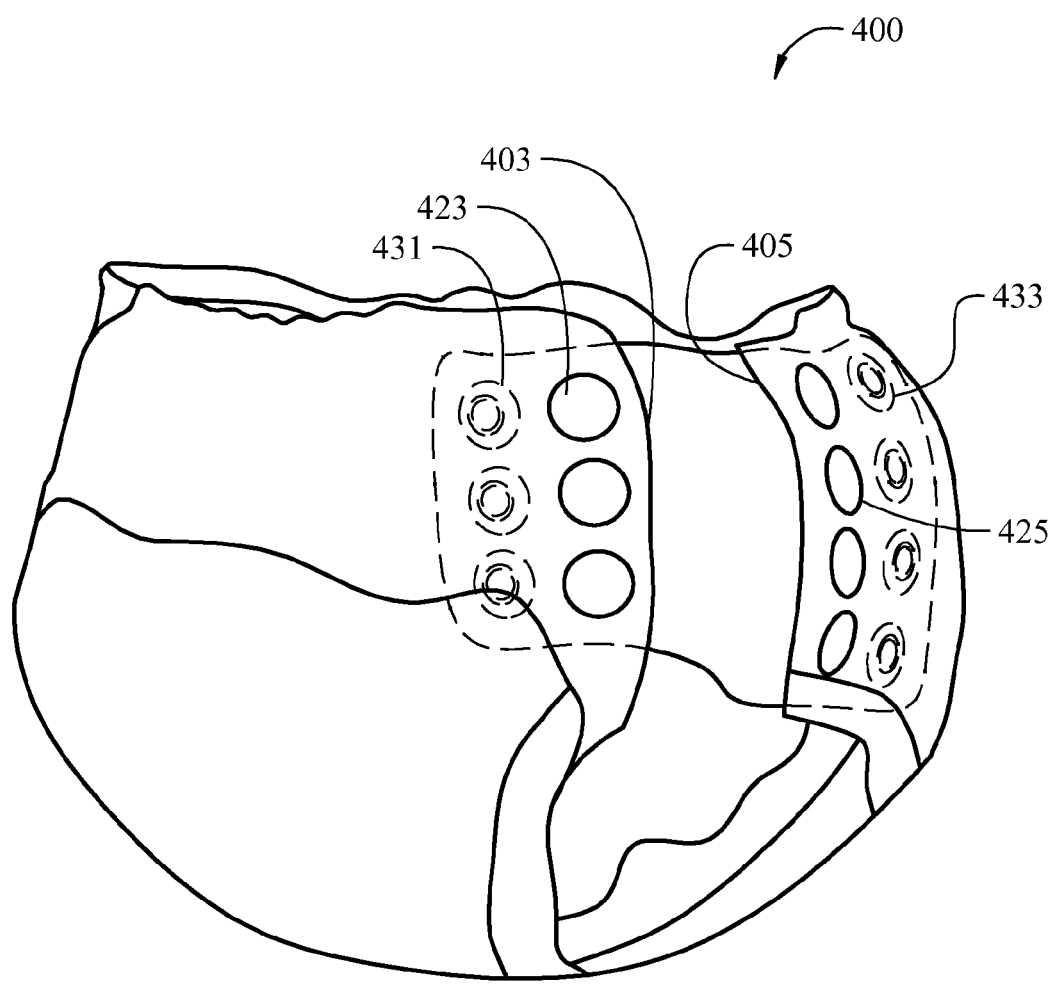

FIG. 16 is another perspective view of the reusable diaper shown in FIG. 13 wherein the intermediate length corner tabs are releasably attached to the reusable diaper and the top and middle rows of snap members along the diaper's forward portion have been snapped together, which thereby reduces the diaper's functional waist size, leg opening size, and functional rise or crotch length as compared to FIG. 15;

FIG. 17 is another perspective view of the reusable diaper shown in FIG. 13 wherein the shortest corner tabs are releasably attached to the reusable diaper and the top and bottom rows of snap members along the diaper's forward portion have been snapped together, which thereby further reduces the diaper's functional waist size, leg opening size, and functional rise or crotch length as compared to that shown in FIG. 16;

FIG. 18 is an exploded perspective view of the reusable diaper shown in FIG. 13 illustrating the interior pockets of the diaper's outer shell (FIG. 18A) and the opposing sides of the liquid-absorbent pad (FIGS. 18B and 18C), wherein the interior pockets are shown in an opened configuration (e.g., pulled back, etc.) to illustrate the exemplary attachment means within the interior pockets by which the liquid-absorbent pad's opposite end portions may be releasable attached within the interior pockets of the outer shell;

FIG. 19 is an exploded perspective view of the reusable diaper shown in FIG. 18 with the liquid-absorbent pad shown releasable attached to the outer shell within the interior pockets and partly folded over itself, which thereby reduces the functional length of the liquid-absorbent pad;

FIG. 20 is another exploded perspective view of the reusable diaper shown in FIG. 18 with the liquid-absorbent pad again shown releasable attached to the outer shell within the interior pockets and partly folded over itself but to a greater degree of overlap than that shown in FIG. 19, which thereby further reduces the functional length of the liquid-absorbent pad as compared to that shown in FIG. 19;

FIG. 21 is a perspective view of the reusable diaper shown in FIG. 19, wherein the portions of the liquid-absorbent pad within the interior pockets are substantially covered by the outermost portions or flaps of the interior pockets, which thereby inhibits contact between those covered portions of the liquid-absorbent pad and the diaper wearer or diaper changer;

FIG. 22 is a perspective view illustrating an interchangeable corner tab having different snap options by which the corner tab may be releasably attached to a reusable diaper thereby providing different functional lengths for the corner tab according to another exemplary embodiment;

FIG. 23 is a perspective view of a reusable diaper having the corner tab shown in FIG. 22, wherein the corner tab is releasably attached via the outermost snap members which are snapped to corresponding snap members within the pockets of the reusable diaper, thereby providing the corner tap with the longest of the functional length options; and FIG. 24 is a perspective view of the reusable diaper shown in FIG. 23, wherein the corner tab is shown releasably attached to the reusable diaper via the corner tab's innermost snap members thereby providing the corner tab with the shortest of the functional length options and also reducing the diaper's functional waist size as compared to FIG. 23.

DETAILED DESCRIPTION

Example embodiments will now be described more fully with reference to the accompanying drawings.

According to various aspects, exemplary embodiments of reusable diapers are disclosed herein. In an exemplary embodiment, a reusable diaper generally includes forward and rearward waist portions. At least one corner tab is releasably attachable to the forward and rearward waist portions, such that the corner tab is detachable and completely separable from the diaper. There is at least one pocket substantially impervious to liquids, which is configured to receive therein at least a portion of the corner tab when the forward and rearward waist portions are releasably attached by the corner tab. The positioning of the portion of the corner tab in the pocket helps inhibit wicking of liquid through the pocket and into the corner tab.

In another exemplary embodiment, a reusable diaper generally includes forward and rearward waist portions. First and second sets of corner tabs are releasably attachable to the forward and rearward waist portions, such that the second set of corner tabs is interchangeable with the first set of corner tabs. The second set of corner tabs sized differently than the first set of corner tabs such that the diaper has a first size when the forward and rearward waist portions are releasably attached by the first set of corner tabs, and such that the diaper has a second size different than the first size when the forward and rearward waist portions are releasably attached by the second set of corner tabs.

In another exemplary embodiment, a reusable diaper generally includes forward and rearward waist portions. A first pocket is disposed in a lateral side portion of the forward waist portion. A second pocket is disposed in an opposite lateral side portion of the forward waist portion. A third pocket is disposed in a lateral side portion of the rearward waist portion. A fourth pocket is disposed in an opposite lateral side portion of the rearward waist portion. First and second pairs of corner tabs each have front and back end portions releasably attachable to the respective forward and rearward waist portions within the respective first, second, third, and fourth pockets, such that the second pair of corner tabs is interchangeable with the first pair of corner tabs. The second pair of corner tabs is sized differently than the first pair of corner tabs. The corner tabs define portions of the waist and leg openings of the diaper when releasably attached to the forward and rearward waist portions, such that interchanging the first and second pairs of corner tabs changes the size of the waist and leg openings of the diaper.

In another exemplary embodiment, a reusable diaper generally includes an inner layer configured to wick moisture from the diaper wearer's body and an outer layer configured to be substantially liquid-impervious. At least one pocket is defined generally by a space between the inner and outer layers. The at least one pocket is configured to receive at least one liquid-absorbent insert therein. The diaper also includes at least one slit in the inner layer that provides access into the space between the inner and outer layers defining the at least one pocket. At least one flap is provided that is positionable in an open configuration or a closed position. When the at least one flap is in the open configuration, the at least one slit is exposed and allows access into the at least one pocket. In the closed configuration, however, the at least one flap substantially covers the at least one slit and inhibits contact between the diaper wearer and at least one liquid-absorbent insert positioned within the at least one pocket. When closed, the at least one flap may also inhibit the inadvertent or accidental removal of the at least one liquid-absorbent insert from the at least one pocket.

In another exemplary embodiment, a reusable diaper generally includes first and second waist portions. The first waist portion includes corner regions that are releasably attachable to the second waist portion. The corner regions may be resiliently stretchable to permit at least some adjustability to the diaper's functional waist size as defined by the first and second waist portions when the first waist portion is releasably attached to the second waist portion.

In another exemplary embodiment, a reusable diaper generally includes a forward portion, a rearward portion, and a crotch portion. The reusable diaper further includes at least a three-by-three array of snap members along the forward portion that allows selective adjustment to the diaper's functional rise or crotch length. The array includes at least a first row of at least three spaced-apart snap members (e.g., plastic male snap members, plastic female snap members, combinations thereof, etc.). The snaps in the first row are vertically spaced from and aligned with corresponding snap members (e.g., plastic female snap members, plastic male snap members, combinations thereof, etc.) in at least two other rows of the array. For example, snap members in a first or top row can be snapped together with the corresponding snap members in the second or middle row to decrease the diaper's functional rise or crotch length. Or, for example, the snap members of the top row can be snapped together with the corresponding snap members in a third or bottom row to even further decrease the diaper's functional rise or crotch length. Advantageously, having at least three columns of snaps may provide a more snug and precise fit to the diaper wearer, for example, by reducing the extent to which the crotch portion hangs down below the wearer. For example, the three-by-three arrangement can eliminate or at least reduce the bulge in the middle front of the diaper that typically occurs when there are only two columns of snaps due to the fabric bulging out between the two snaps. The three-by-three snap arrangement may enable the diaper to be more of a one-size fits all cloth diaper. Alternative embodiments may include more or less than three rows of snaps, more or less than three columns of snaps, and/or different connector members besides snaps.

In some embodiments, a reusable diaper may include at least one inner liner or layer. The at least one inner layer can be configured to wick moisture from the diaper wearer's body generally towards the at least one liquid-absorbent insert within the at least one pocket. The reusable diaper may further comprise at least one outer layer or liner along at least an outer portion of the reusable diaper. The at least one outer layer can be substantially liquid-impervious to thereby resist wicking of moisture through the at least one outer layer. In some preferred embodiments, the outer layer is formed of polyester, and the inner layer is formed of suede cloth. Alternatively, other suitable materials may be used for the inner and/or outer layers.

In some embodiments, there may be provided a plurality of replacement liquid-absorbent inserts. In such embodiments, an existing liquid-absorbent insert may be removed from a pocket after the insert has become saturated. One of the replacement inserts can be positioned within the pocket after the diaper has been washed or laundered.

Other embodiments of a reusable diaper may include a first waist portion having corner regions with tabs releasably attachable to a second waist portion. The corner regions may be resiliently stretchable to permit some adjustability to the functional waist size of the reusable diaper as defined by the first and second waist portions. In some embodiments, the corner regions may be formed from 95% polyester and 5% Lycra. Alternatively, the corner regions may be formed using other suitable materials. The tabs may also be releasably attachable to an interior portion of the diaper (e.g., to a back side of a flap, etc.) for retaining the corner regions and tabs within the interior of the reusable diaper. A wide range of attachment means may be used for releasably attaching the tabs to the second waist region and/or to an interior portion of the diaper, such as hook-and-loop fasteners, snaps, buttons, adhesives, combinations thereof, etc.

Referring now to FIGS. 1 through 6, there is shown an exemplary embodiment of a reusable diaper 100 embodying one or more aspects of the present disclosure. As shown, the reusable diaper 100 includes a first waist portion or region 110, a second waist portion or region 112, and a crotch portion or region 114 disposed generally between the first and second waist portions 110, 112. The first waist portion 110 includes corner regions 116 and 118. The second waist portion 112 includes corner regions 120 and 122.

Figure 2:
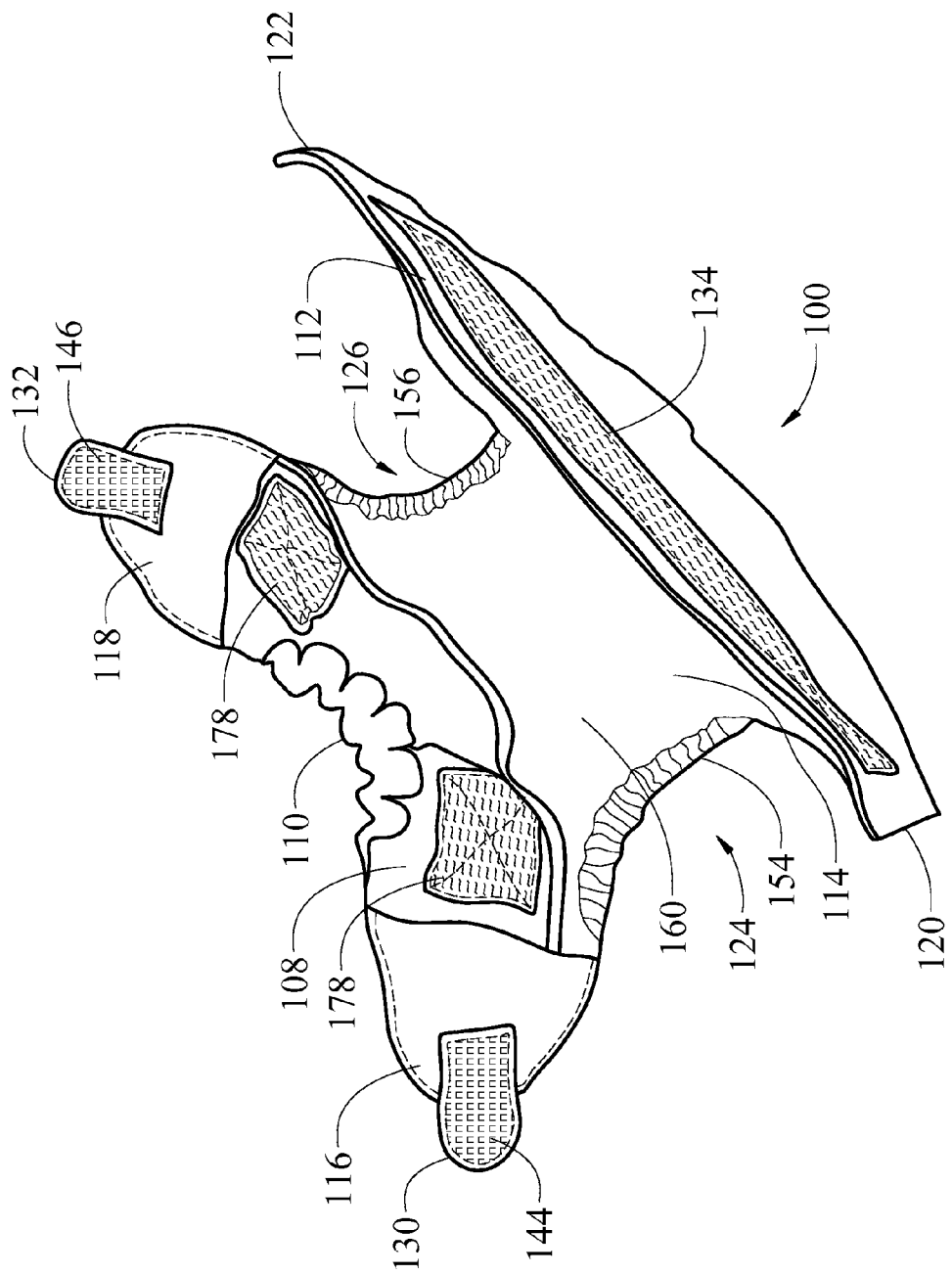
FIG. 2 is a perspective view of the reusable diaper shown in FIG. 1, wherein the flap is shown in a closed configuration in which the flap substantially covers the opening into the pocket and inhibits contact between the diaper wearer and the liquid-absorbent insert positioned within the pocket.
Figure 3:
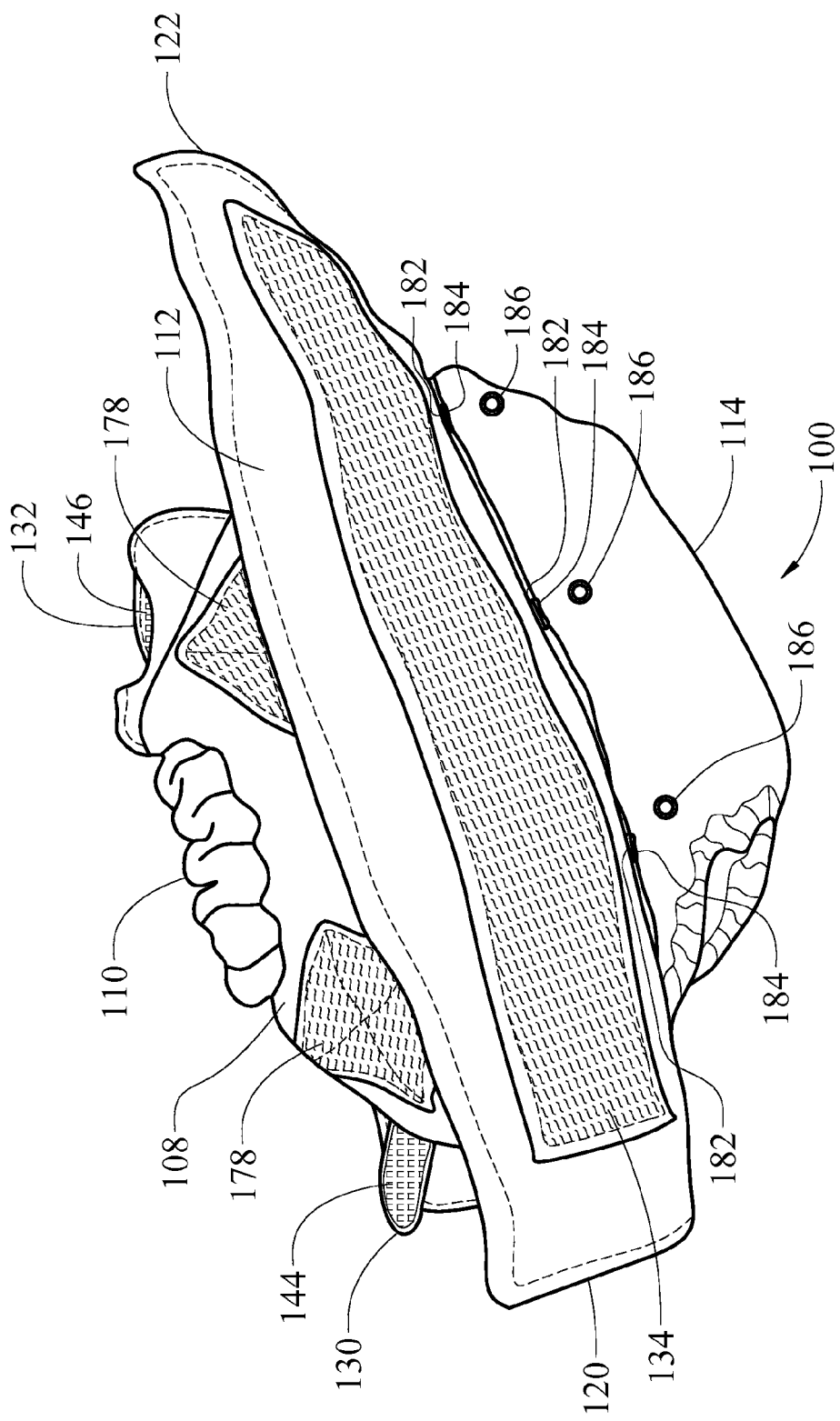
FIG. 3 is a front perspective view of the reusable diaper shown in FIGS. 1 and 2, wherein the top row of snap members have been snapped into the corresponding snap members in the middle row thereby reducing the diaper's functional rise or crotch length.
Figure 4:
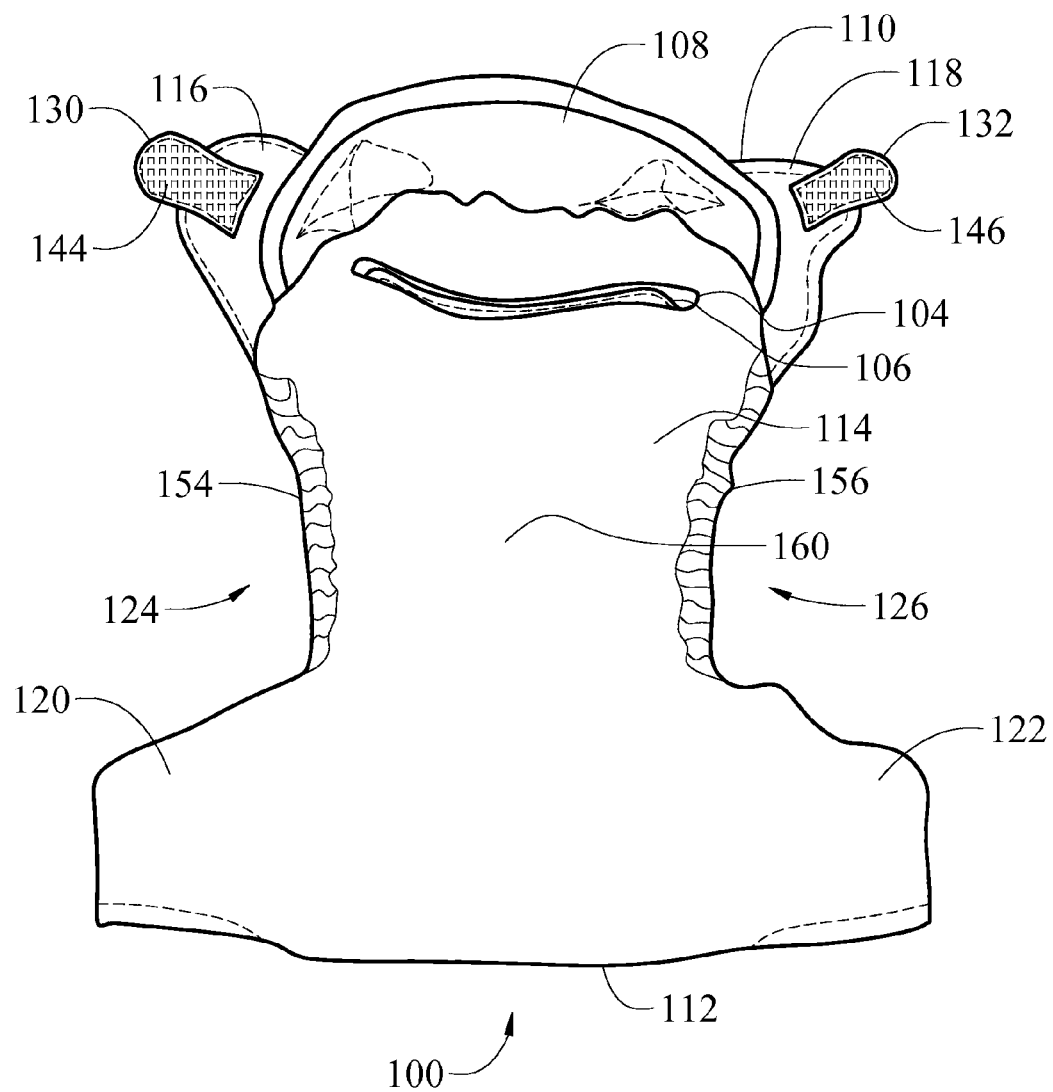
FIG. 4 is an inner view of the reusable diaper shown in FIGS. 1 through 3.

As shown in FIG. 2, the contours of the corner regions 116, 118, 120, 122 and crotch portion 114 cooperatively define leg openings 124 and 126. For example, leg opening 124 is cooperatively defined by the curve extending from the first waist portion's corner region 116 along the crotch portion 114 to the second waist portion's corner region 120. In addition, the other leg opening 126 is defined by the curve extending from the first waist portion's corner region 118 along the crotch portion 114 to the second waist portion's corner region 122. In this illustrated embodiment, the leg openings 124 and 126 may further comprise elastic disposed adjacent the periphery of the leg openings 124 and 126, for example, to help draw and hold the diaper 100 against the wearer's legs.

Figure 1:
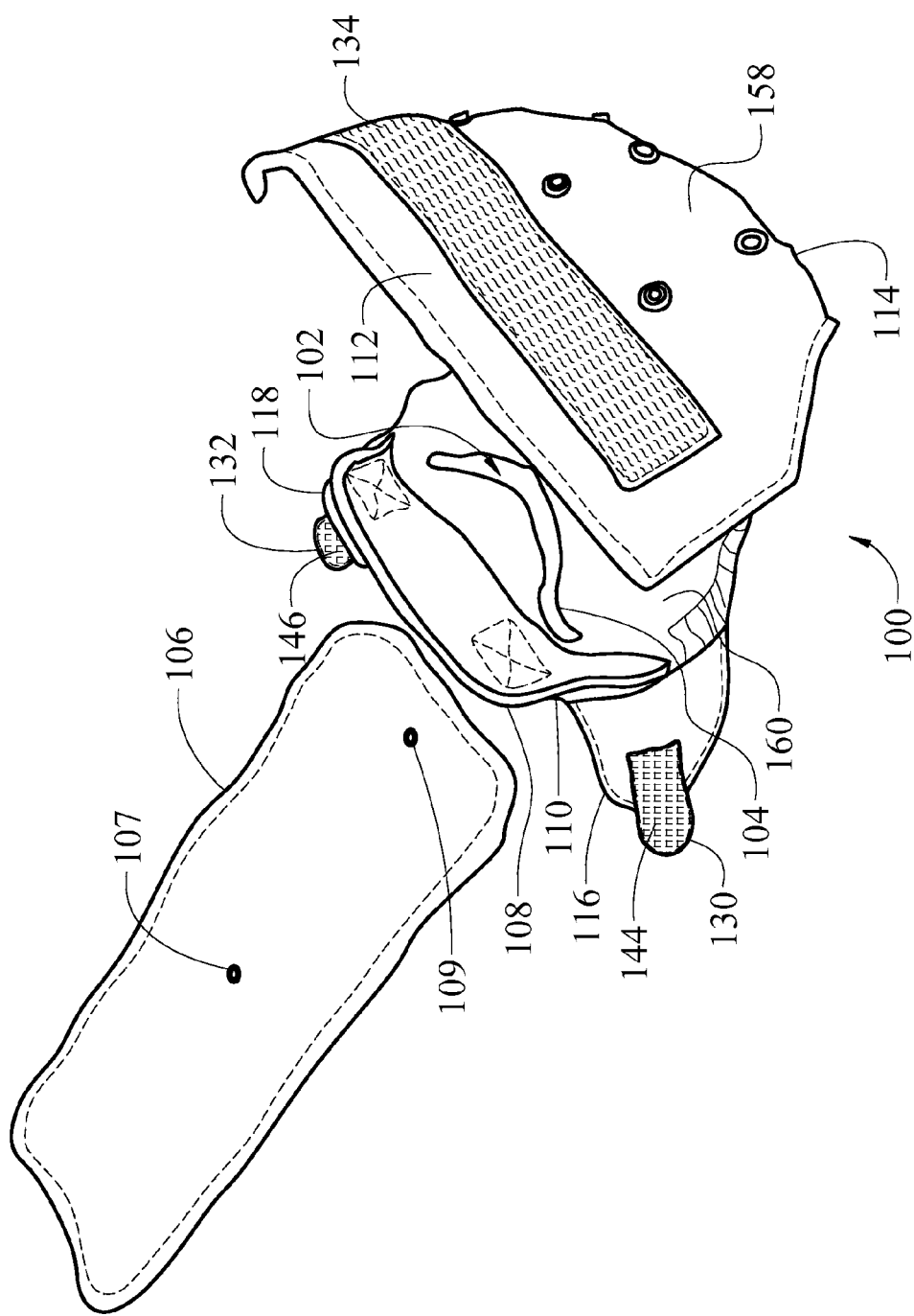
FIG. 1 is an exploded perspective view of a reusable diaper having a pocket opening and a flap according to exemplary embodiments, wherein the flap is shown in an opened configuration in which the opening into the pocket is exposed to allow a liquid-absorbent insert to be positioned within the pocket.
Figure 5:
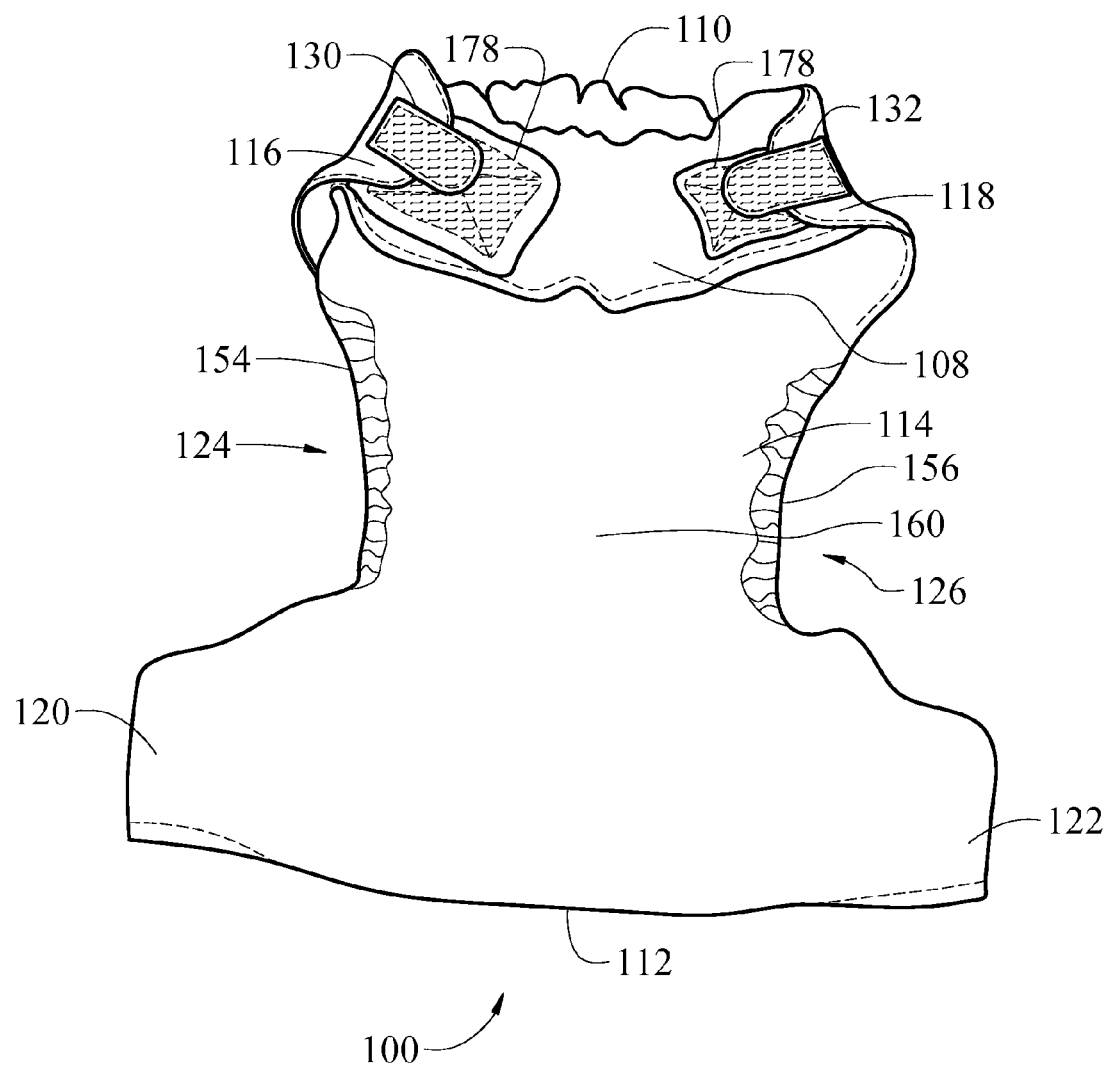
FIG. 5 is an inner view of the reusable diaper shown in FIG. 4, wherein tabs have been releasably attached to the flap with hook-and-loop fasteners.

With continued reference to FIG. 1, the reusable diaper 100 includes a pocket 102 defined generally by the space between the diaper's outer layer 158 and inner layer 160. The diaper 100 also includes an opening or slit 104 in the inner layer 160 that allows access into the pocket 102. The reusable diaper 100 further includes a flap 108 positionable in either an open configuration (FIGS. 1 and 4) or a closed configuration (FIGS. 2 and 5).

When the flap 108 is in the open configuration, the slit 104 is exposed and allows access into the pocket 102. In the closed configuration, however, the flap 108 substantially covers the slit 104 and inhibits contact between the skin or clothes of the diaper wearer and the liquid-absorbent insert 106 positioned within the pocket 102. Additionally, closing the flap 108 may also inhibit the inadvertent or accidental removal of the insert 106 from the pocket 102. In alternative embodiments, a suitable attachment means may be employed for releasably retaining the flap in the closed position, such as hook-and-loop fasteners, snaps, adhesives, buttons, clasps, magnets, combinations thereof, etc.

The flap 108 may be formed from a wide variety of materials. In some preferred embodiments, the flap 108 is formed from one or more fabric materials, such as suede cloth, etc. In such embodiments, the flap 108 and the inner layer 160 may formed from the same materials. Alternatively, the flap 108 and inner layer 160 may be formed from different materials.

The flap 108 may be attached to the reusable diaper 100 using a wide variety of attachment methods, such as stitching, sewing, adhesive attachment, integrally formed, etc. In some preferred embodiments, the flap 108 is attached to the inner layer 160 along the diaper's rear portion by stitching or sewing. In such embodiments, the flap 108 and opening 104 into the pocket 102 are not readily accessible by the diaper wearer.

As shown in FIG. 1, a liquid-absorbent insert 106 can be received within the pocket 102 via the slit 104. The insert 106 is preferably configured to absorb and store liquids therein. The insert 106 may comprise one or more of microfibers, hemp, hydrocolloid materials, or any other suitable material configured to absorb and store liquids therein.

In this particular embodiment, the insert 106 is shown with snap members 107 and 109. These snap members 107, 109 can be snapped together or unsnapped to thereby allow selective adjustment to the length of the insert 106. For example, the snap member 107 can be snapped together with the snap member 109 to decrease the insert's length. Or, for example, the snap members 107 and 109 can be unsnapped to increase the insert's length. This lengthwise adjustability can allow the insert 106 to more precisely fit within the pocket 102, for example, when the functional rise or crotch length of the diaper is changed by way of the array of snaps 180 (as described in more detail below). Alternative embodiments may include an insert having more or less snaps and/or snaps in other arrangements to accommodate lengthwise adjustability to the insert. Further embodiments may include an insert having a wide range of other suitable fastening means or fastening systems besides snaps, such as adhesives, buttons, clasps, Velcro® hook and loop closures, magnets, elastic straps, adjustable straps, combinations thereof, etc.

In the illustrated embodiment, the pocket 104 is defined generally by the space between the diaper's outer layer 158 and inner layer 160. The pocket's periphery or perimeter is defined to extend generally from about the first waist portion 110 along the first and second edge portions 154, 156 of the crotch region 114 to about the second waist portion 112. Stitching (or other suitable means) may be used to secure the perimeter or periphery of the pocket 102. For example, the illustrated embodiment has the pocket periphery formed generally by the same stitching used to attach the outer and inner layers 160, 158 to each other.

A wide range of suitable materials may be used for the inner and outer layers 160, 158. The inner layer 160 is preferably configured to wick moisture generally away from the diaper wearer towards the insert 106 within the pocket 102. The outer layer 158 is preferably configured to be substantially liquid-impervious to thereby resist wicking of moisture through the outer layer 158. In one preferred embodiment, the outer layer 158 is formed of polyester, and the inner layer 160 is formed of suede cloth. Alternatively, other suitable materials may be used for the inner liner and/or outer layers 160, 158.

Accordingly, the reusable diaper 100 may be put on a wearer with the inner layer 160 positioned against the skin of the wearer. In which case, the inner layer 160 can wick moisture (e.g., bodily discharge, urine, sweat, etc.) through the inner layer 160 to the liquid-absorbent insert 106 within the pocket 102. When the insert 106 has become saturated, the insert 106 may be removed and then washed or laundered along with or separately from the diaper 100. After the diaper 100 and insert 106 have been satisfactorily washed and dried, the insert 106 may be repositioned within the pocket 102 of the diaper 100. At which point, the diaper 100 may be reused.

In some preferred embodiments, the first waist portion's corner regions 116 and 118 are resiliently stretchable. This feature allows at least some adjustability to the diaper's functional waist size as defined by the first and second waist portions 110 and 112 when the first waist portion 110 is releasably attached to the second waist portion 112. In some embodiments, the corner regions may be formed from 95% polyester and 5% Lycra. Alternatively, the corner regions may be formed using other suitable materials.

With reference to FIG. 2, the reusable diaper 100 includes tabs 130, 132 associated with the first waist portion 110. In addition to stretchable corner regions, some embodiments also configure the tabs 130, 132 to be resiliently elastic or stretchable. This, in turn, can permit further adjustability to the diaper's functional waist size. In yet other embodiments, only the tabs 130 and 132 are resiliently elastic or stretchable. In further embodiments, however, the tabs 130, 132 may be essentially inelastic or stretchable.

The tabs 130, 132 may include respective hook-and-loop fastener portions 144, 146, which, in turn, are releasably attachable to corresponding hook-and-loop fastener portions of the second waist portion 112. As shown in FIG. 2, the second waist portion 112 includes an elongate strip 134 having hook-and-loop fasteners portions extending along the length thereof. Accordingly, the hook-and-loop fastener portions 144, 146 of the tabs 130, 132, respectively, can be releasably attachable at different locations along the elongate strip 134, which allows the first waist portion 110 to be adjustably secured to the second waist portion 112 when positioned around a wearer of the reusable diaper 100.

Having resiliently elastic or stretchable corner regions 116, 118 (and/or tabs 130, 132 in some embodiments) with the ability to stretch can allow for tailoring of the diaper's functional waist size to the wearer's actual waist size. For example, the diaper's functional waist size may be selectively tailored for the wearer by stretching the corner regions 116, 118, and then releasably attaching the tabs 130, 132 to the elongate strip 134 at particular attachment locations along the length of the elongate strip 134. In this exemplary manner, the diaper's functional waist size can be selectively adjusted, for example, to provide a relatively snug fit about the waist of the wearer (e.g., infant, toddler, adult, etc.), and preferably without being too uncomfortably tight about the wearer's thighs. Alternative embodiments may include other suitable means for allowing selective adjustment to the functional or operational waist size of the reusable diaper. In addition, other suitable fastening means or fastening systems may also be employed for releasably attaching the diaper's first and second waist portions to each other, such as different hook-and-loop fastener arrangements (e.g., two or more spaced-apart discrete patches along the second waist portion instead of a single elongate strip, etc.), adhesives, snaps, buttons, clasps, Velcro® hook and loop closures, magnets, combinations thereof, etc.

In some embodiments, the tabs 130, 132 may be releasably attachable to an interior portion of the diaper for retaining the corner regions and tabs within the interior of the reusable diaper. As shown in FIG. 2, the tabs 130, 132 include hook-and-loop fastener portions 144, 146 releasably attachable to corresponding hook-and-loop fastener portions 178 of the flap 108. Releasably attaching the tabs 130 and 132 to the flap 108 by way of the hook-and-loop fastener portions 144, 146, 178 (FIG. 5) helps retain the tabs 130 and 132 and corner regions 116 and 118 within an interior of the diaper 100. This, in turn, may help to prevent or at least reduce snagging of the tabs 130, 132 when the reusable diaper 100 is being washed or laundered. Alternatively, a wide range of other attachment means may be used for releasably attaching the tabs 130, 132 to an interior portion of the diaper, such as hook-and-loop fasteners, snaps, buttons, adhesives, combinations thereof, etc.

In some embodiments, the tabs 130, 132 may be releasably attachable to each other. For example, one of the tabs 130 or 132 may have a forward surface with hook-and-loop fasteners that are releasably attachable to hook-and-look fasteners on a rearward surface of the other tab 130 or 132. Alternatively, other suitable fastening means can be employed to implement this feature.

Figure 6:
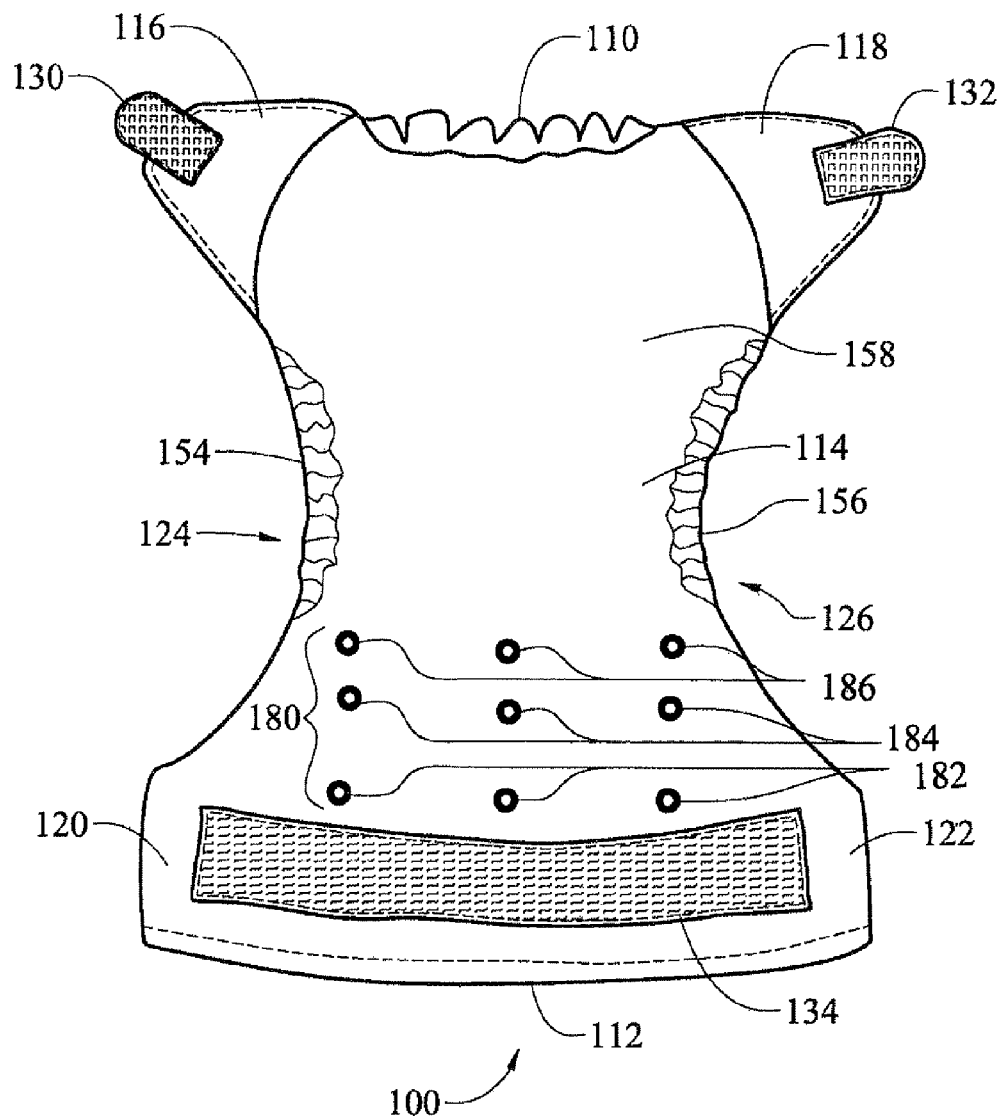
FIG. 6 is an outer view of the reusable diaper shown in FIGS. 1 through 5.

With reference to FIG. 6, the reusable diaper 100 includes snaps that allow for customization or adjustment to the diaper's functional rise or crotch length. This feature may help create an even better or snugger fit to the diaper wearer. For example, the snaps can allow for a reduction in the diaper's functional rise or crotch length so as to reduce the extent to which the crotch portion 114 hangs down below the wearer.

As shown in FIG. 6, the diaper 100 includes a three-by-three array 180 of snap members. The snap members comprising the three-by-three array 180 are horizontally arranged and aligned in the three rows and vertically arranged and aligned in the three columns. Advantageously, having at least three columns may provide a more snug and precise fit to the diaper wearer, for example, by reducing the extent to which the crotch portion hangs down below the wearer. The three-by-three arrangement can eliminate or at least reduce the bulge in the middle front of the diaper that typically occurs when there are only two columns of snaps due to the fabric bulging out between the two snaps. The three-by-three snap arrangement may enable the diaper to be more of a one-size fits all cloth diaper.

In the illustrated embodiment, the first row includes three spaced-apart male snap members 182. The second or middle row includes three spaced-apart female snap members 184. The third row includes three-spaced apart female snap members 186. The first row of snap members 182 is vertically spaced from and aligned with the corresponding snap members 184, 186 in the two other rows of the array 180. Each row of snap members includes a first snap member located generally centrally across a width of the diaper 100, a second snap member located toward one lateral side of the diaper 100, and a third snap member located toward another lateral side of the diaper 100

The male snap members 182 can be snapped together with either the female snap members 184 of the second row, or the female snap members 186 of the third row. For example, the male snap members 182 in the first row can be snapped together with the corresponding female snap members 184 in the second or middle row to decrease the diaper's functional rise or crotch length. To decrease the diaper's functional rise and crotch length to an even greater extent, the male snap members 182 of the first row may instead be snapped together with the corresponding female snap members 186 in the third row. Accordingly, these snap options thus provide three different configurations for the diaper 100. That is, the functional rise or crotch length of the reusable diaper 100 can be changed by selectively choosing whether to engage the male snap members 182 with the female snap members 184 or the female snap members 184, or by simply choosing to do neither.

In some preferred embodiments, the snap members 182, 184, 186 are plastic. Alternatively, the snap members can be formed from other materials, which are preferably relatively lightweight and durable to withstand repeated laundry cycles.

In alternative embodiments, a reusable diaper may include more or less snap options and/or snap members in other arrangements than what is shown in FIG. 6. For example, another embodiment may include two rows of male snap members with only one row of female snap members. As another example embodiment, a diaper may include a row having both male and female snap members. Additional examples include diapers having more or less than three rows of snap members and/or more or less than three columns of snap members. Still further embodiments may include a wide range of other suitable fastening means or fastening systems besides snaps, such as adhesives, buttons, clasps, Velcro® hook and loop closures, magnets, elastic straps, adjustable straps, combinations thereof, etc.

In some embodiments, a reusable diaper may also include a foldable front portion along the second waist portion. This foldable front portion may be folded down, for example, to help keep the umbilical area of the diaper wearer clean.

Figure 7:
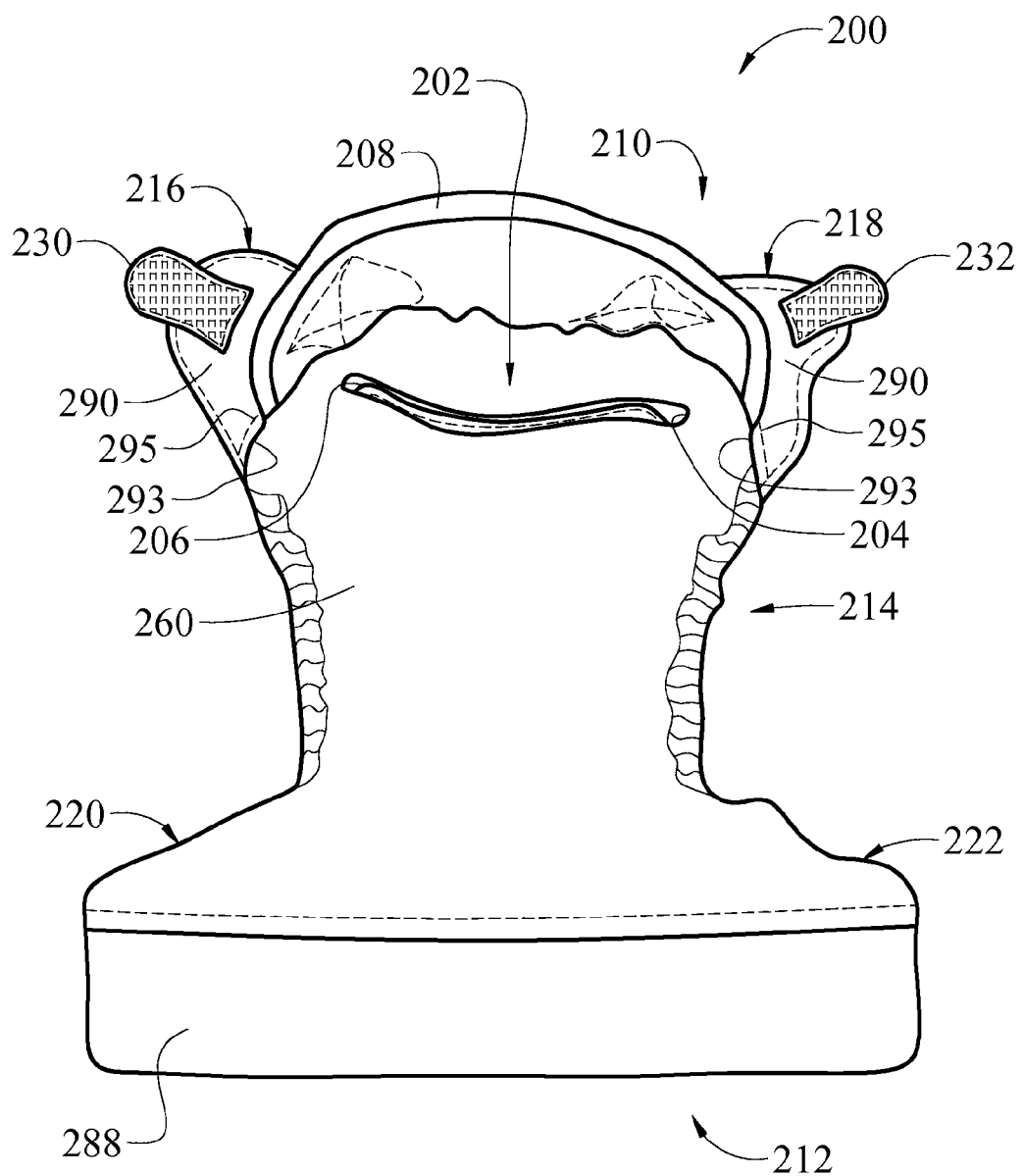
FIG. 7 is an inner view of another exemplary embodiment of a reusable diaper.
Figure 8:
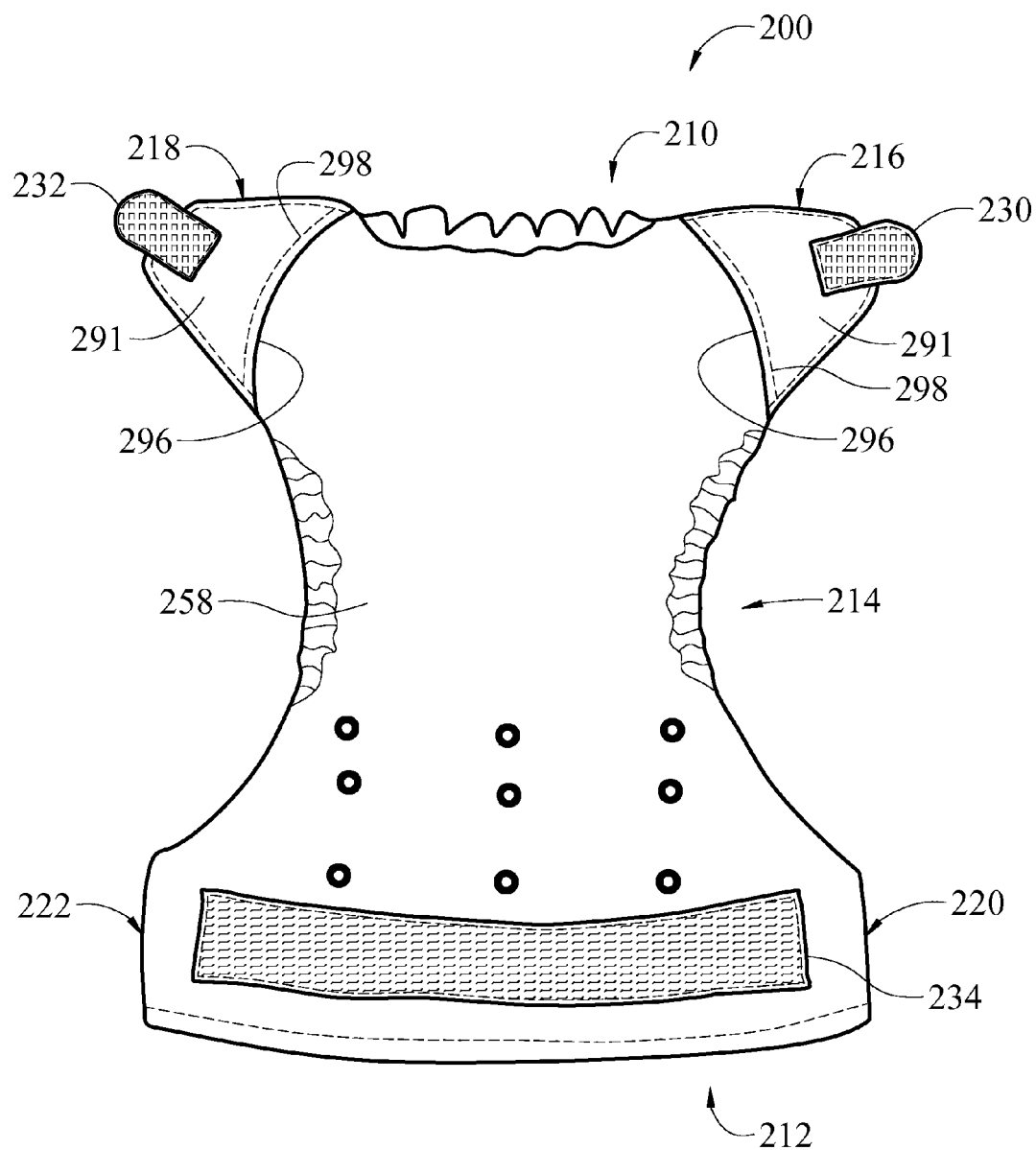
FIG. 8 is an outer view of the reusable diaper shown in FIG. 7.

FIGS. 7-12 illustrate another exemplary embodiment of a reusable diaper (indicated generally at 200) embodying one or more aspects of the present disclosure. As shown in FIGS. 7 and 8, the reusable diaper 200 generally includes a first waist portion 210 (e.g., a rearward waist portion, etc.), a second waist portion 212 (e.g., a forward waist portion, etc.), and a crotch portion or region 214 disposed generally between the first and second waist portions 210, 212. The first waist portion 210 includes corner regions 216, 218 which are releasably attachable to the second waist portion 212 to secure the reusable diaper 200 in a desired position. More particularly, tabs 230, 232 of the respective corner regions 216, 218 are releasably attachable (e.g., via corresponding hook-and-loop fasteners, etc.) to an elongate strip 234 of the second waist portion 212 (FIG. 8) to secure the diaper in a desired position (e.g., around a wearer, with the wearer generally in contact with an inner layer 260 of the reusable diaper 200, etc.).

The corner regions 216, 218 of the first waist portion 210 may be resiliently stretchable. This feature allows for at least some adjustability of the diaper's functional waist size as defined by the first and second waist portions 210, 212 when the first waist portion 210 is releasably attached to the second waist portion 212. Moreover, the resiliently stretchable corner regions 216, 218 may be substantially impervious to fluids. For example, the resiliently stretchable corner regions 216, 218 may be at least partially coated, treated, etc. with durable water repellant to make them substantially impervious to liquids. Any suitable durable water repellant may be used within the scope of the present disclosure. In other exemplary embodiments, reusable diapers may include resiliently stretchable corner regions having other suitable materials, coatings, etc. applied thereto to make the resiliently stretchable corner regions substantially impervious to liquids.

With continued reference to FIGS. 7 and 8, the reusable diaper 200 also includes an outer layer 258 and the inner layer 260. The outer layer 258 and the inner layer 260 may broadly be viewed as defining at least part of the first and second waist portions 210, 212. The outer layer 258 may be configured to be substantially liquid-impervious to thereby resist wicking of moisture through the outer layer 258, and may be formed, for example, of polyester, nylon, spandex, combinations thereof, etc. The inner layer 260 may be configured to wick moisture generally away, for example, from a diaper wearer, and may be formed, for example, of suede cloth, polyester suede cloth, micro fleece, other forms of fabric designed to wick moisture, combinations thereof, etc. A pocket 202 is defined generally by the space between the diaper's outer layer 258 and inner layer 260. The pocket 202 is configured (e.g., sized, shaped, constructed, etc.) to receive at least one liquid-absorbent insert 206 therein, for example, for help in absorbing and storing liquids (e.g., moisture wicked away from a diaper wearer, etc.). An opening or slit 204 is formed in the inner layer 260 to allow access into the pocket 202, and a flap 208 coupled generally to the first waist portion 210 can be positioned to cover the slit 204 and help retain the liquid-absorbent insert 206 within the pocket 202 as desired.

The reusable diaper 200 may further include one or more fluid-resistant regions that, for example, may help resist wicking of moisture through the diaper 200 past the one or more fluid-resistant regions. In the illustrated reusable diaper 200, the inner layer 260 includes a fluid-resistant region disposed adjacent the second waist portion 212. More particularly in the illustrated reusable diaper 200, and as best shown in FIG. 7, the fluid-resistant region includes a strip 288 coupled (e.g., seamed, stitched, etc.) to both the inner layer 260 and the outer layer 258. Here, the fluid-resistant strip 288 may be viewed as defining at least part of the first waist portion 212. The fluid-resistant strip 288 extends generally across a width of the inner layer 260 substantially from one corner region 220 of the second waist portion 212 to another corner region 222 of the second waist portion 212. This may substantially resist wicking of moisture through the inner layer 260 past the fluid-resistant strip 288. It should be appreciated that a wide range of suitable materials, coatings, laminates, etc. may be used for the fluid-resistant strip 288, including, for example, polyester materials, durable water repellant coatings, etc.

As previously stated, the one or more fluid-resistant regions (e.g., the fluid-resistant strip 288, etc.) of the illustrated reusable diaper 200 may help resist wicking of moisture through the diaper 200 past the one or more fluid-resistant regions. In the illustrated embodiment, for example, the fluid-resistant strip 288 is disposed adjacent the second waist portion 212 and may help prevent wicking of moisture from the reusable diaper 200 (e.g., from the liquid-absorbent insert 206 received within the pocket 202 of the reusable diaper 200, from the inner layer 260 of the reusable diaper 200, etc.) to a shirt, blanket, article of bedding, etc. that may come into contact with a part of the first waist portion 212 (e.g., an inner part of the first waist portion 212, etc.). In other exemplary embodiments, reusable diapers may include inner layers having fluid-resistant regions shaped differently than disclosed herein; having fluid-resistant regions disposed, located, etc. differently than disclosed herein; having fluid-resistant regions with one or more separated parts; etc. For example, in one exemplary embodiment, fluid-resistant regions may be disposed adjacent one or more of waist portions, leg regions, etc. of reusable diapers. In one exemplary embodiment, fluid-resistant regions are disposed adjacent both first and second waist portions of a reusable diaper.

With additional reference now to FIGS. 9-12, the resiliently stretchable corner regions 216, 218 of the first waist portion 210 of the reusable diaper 200 will be described. FIGS. 9-12 illustrate the resiliently stretchable corner region 216 with it understood that a description of the resiliently stretchable corner region 218 would be substantially the same (similar reference numbers are thus used in the figures for corresponding parts of the resiliently stretchable corner regions 216, 218). As shown, the resiliently stretchable corner region 216 includes a first layer 290 and a second layer 291, which are coupled together to define an interior region/portion 292 (FIGS. 11 and 12) of the corner region 216. In the illustrated embodiment, the first layer 290 and the second layer 291 are coupled via stitches. Alternatively, other suitable methods, materials, etc. may be used to couple the first and second layers 290, 291 together to define the interior portion 292 (e.g., epoxy, hot-melt processes, etc.).

Figure 9A:
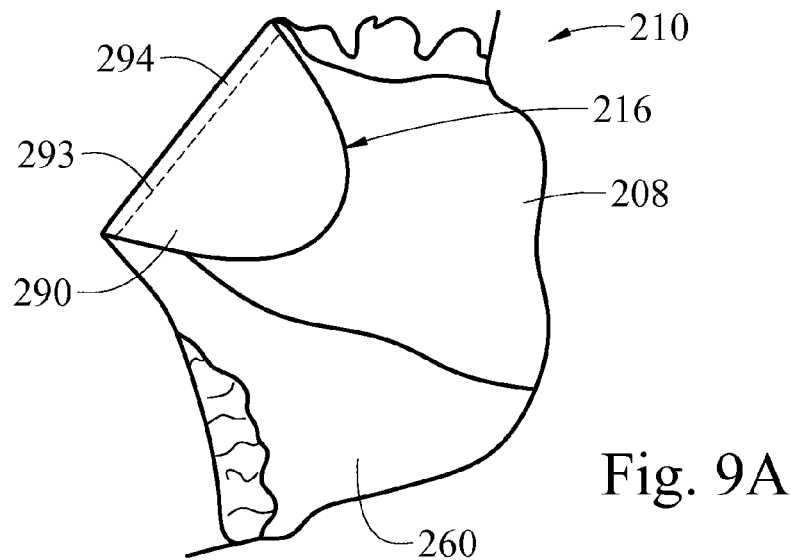
FIG. 9A is a fragmentary inner view of the reusable diaper shown in FIG. 7 illustrating a first seam allowance formed when stitching a first layer of a corner region to a flap and an inner layer of the reusable diaper.
Figure 9B:
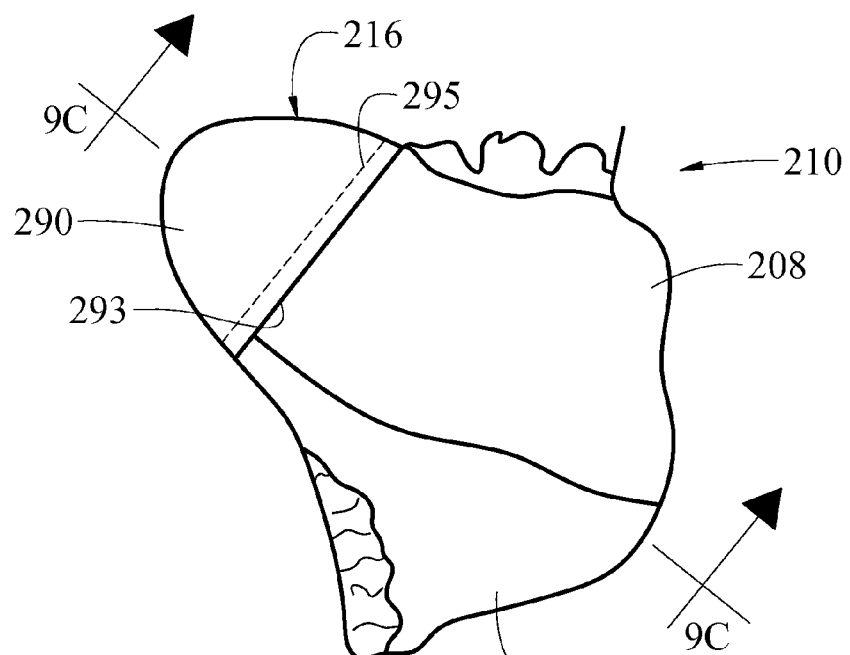
FIG. 9B is a view similar to FIG. 9A illustrating the first seam allowance stitched to the first layer of the corner region.
Figure 9C:
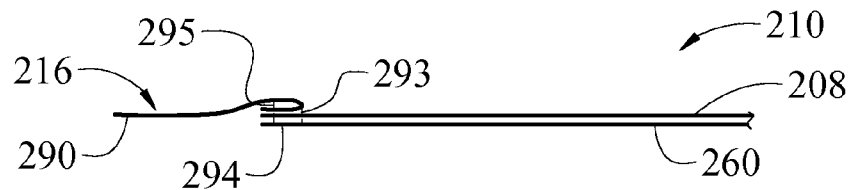
FIG. 9C is a section view taken in a plane including line 9C-9C in FIG. 9B.

As best shown in FIGS. 7 and 9A-9C, the first layer 290 of the illustrated corner region 216 is also coupled to the flap 208 and the inner layer 260 of the reusable diaper 200. To do so, edge margins of the first layer 290, the flap 208, and the inner layer 260 may first be generally aligned such that the first layer 290, the flap 208, and the inner layer 260 are in a generally overlapped position (FIG. 9A). A stitch 293 may then be positioned through the first layer 290, the flap 208, and the inner layer 260 adjacent their generally aligned edge margins to couple them together. This defines a first seam allowance 294 between the stitch 293 and the edge margins of the first layer 290, the flap 208, and the inner layer 260. The first layer 290 may then be folded at the stitch 293 so as to overlap the first seam allowance 294. And a top-stitch 295 may then be positioned through the folded first layer 290 and the first seam allowance 294 (FIGS. 9B and 9C) to couple the first seam allowance 294 to the first layer 290.

Figure 10A:
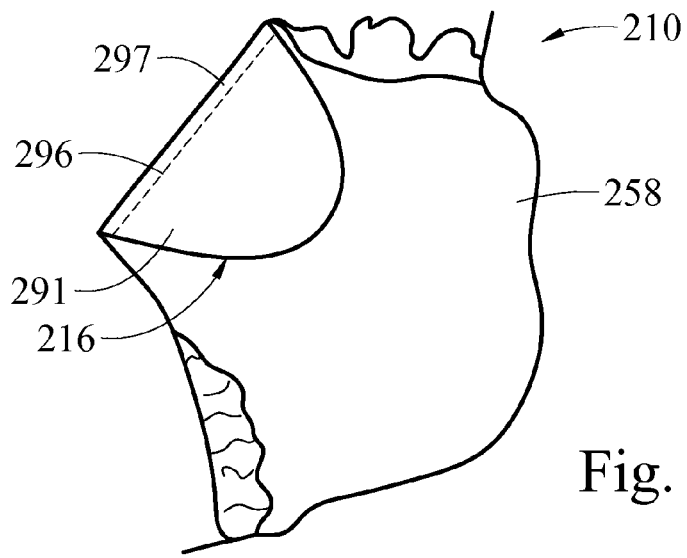
FIG. 10A is a fragmentary outer view of the reusable diaper shown in FIG. 7 illustrating a second seam allowance formed when stitching a second layer of a corner region to an outer layer of the reusable diaper.
Figure 10B:
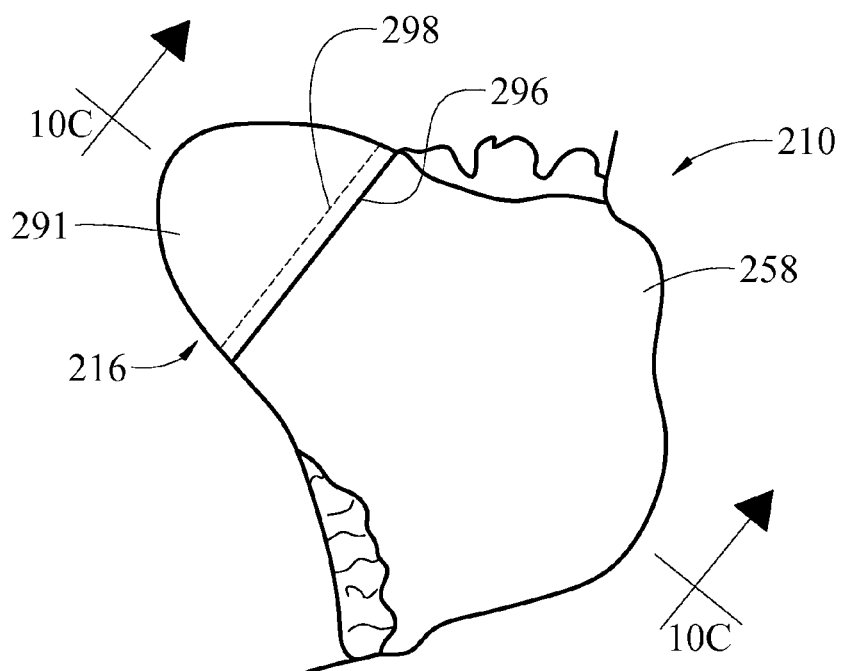
FIG. 10B is a view similar to FIG. 10A illustrating the second seam allowance stitched to the second layer of the corner region.
Figure 10C:
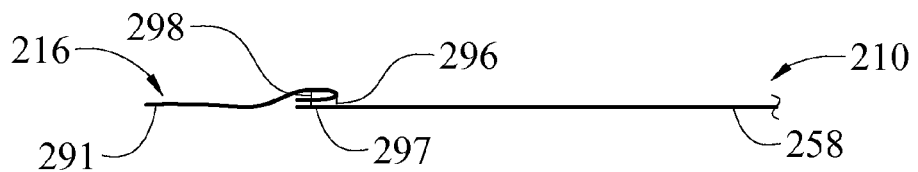
FIG. 10C is a section view taken in a plane including line 10C-10C in FIG. 10B.

As best shown in FIGS. 8 and 10A-10C, the second layer 291 of the corner region 216 is also coupled to the outer layer 258 of the reusable diaper 200. To do so, edge margins of the second layer 291 and the outer layer 258 may first be generally aligned such that the second layer 291 and the outer layer 258 are in a generally overlapped position (FIG. 10A). A stitch 296 may then be positioned through the second layer 291 and the outer layer 258 adjacent their generally aligned edge margins to couple them together. This defines a second seam allowance 297 between the stitch 296 and the edge margins of the second layer 291 and the outer layer 258. The second layer 291 may then be folded at the stitch 296 so as to overlap the second seam allowance 297. And a top-stitch 298 may then be positioned through the folded second layer 291 and the second seam allowance 297 (FIGS. 10B and 10C) to couple the second seam allowance 297 to the second layer 291.

It should be appreciated that at least part of the flap 208, the inner layer 260, and the outer layer 258 may be coupled together before the first and second layers 290, 291 of the corner region 216 are coupled thereto. Alternatively, the first and second layers 290, 291 of the corner region 216 may be coupled to the respective flap 208, inner layer 260, and outer layer 258 of the reusable diaper 200 before the flap 208, inner layer 260, and outer layer 258 are coupled together within the scope of the present disclosure. In addition in other exemplary embodiments, three or more stitches may be used to couple first and second layers of corner regions to respective flaps, inner layers, and outer layers of reusable diapers. In still other exemplary embodiments, reusable diapers may have corner regions coupled thereto other than by stitching (e.g., by epoxy, by hot-melt processes, etc.).

Figure 11:
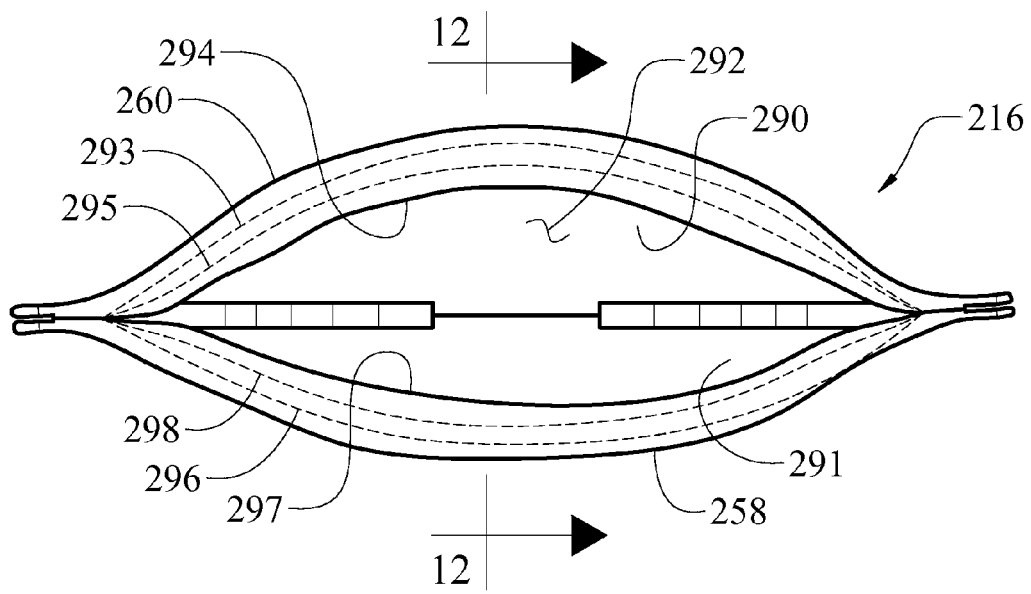
FIG. 11 is a fragmentary view of a corner region of the reusable diaper shown in FIG. 7 illustrating an interior portion of the corner region with first and second seam allowances disposed generally within the interior portion of the corner region.
Figure 12:
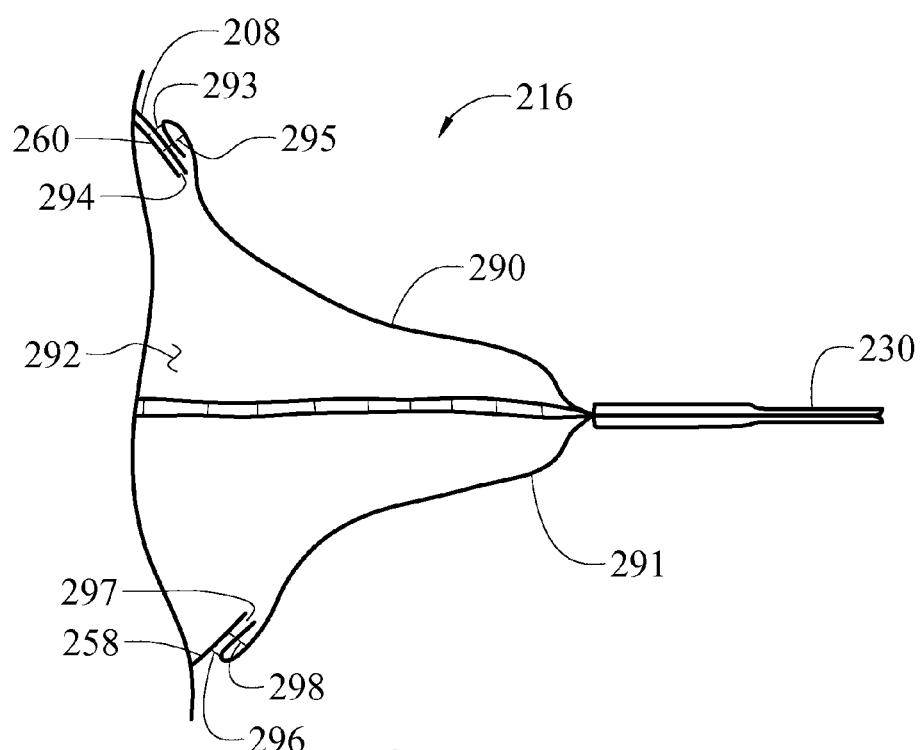
FIG. 12 is a section view taken in a plane including line 12-12 in FIG. 11.

With particular reference now to FIGS. 11 and 12, the first and second seam allowances 294, 297 (when coupled to the respective first and second layers 290, 291 of the corner region 216) are positioned generally within the interior portion 292 of the corner region 216. In this position, the first and second seam allowances 294, 297 each extend generally away from the respective outer layer 258 and inner layer 260 of the reusable diaper 200 (and away from the pocket 202 formed between the outer layer 258 and the inner layer 260). This may help inhibit wicking of liquid through the first and second seam allowances 294, 297 to the corner region 216. For example, in the illustrated reusable diaper 200, moisture moving through the reusable diaper 200 (e.g., through the liquid-absorbent insert 206 received within the pocket 202 formed between the outer and inner layers 258, 260; through the inner layer 260; along the substantially liquid-impervious outer layer 258; etc.) may approach the corner region 216 (as well as the corner region 218) of the first waist portion 210. But the positioning of the first and second seam allowances 294, 297 generally facing away from the moisture transporting regions of the reusable diaper 200 (e.g., the liquid-absorbent insert 206; the inner layer 260; along the substantially liquid-impervious outer layer 258; etc.) may help inhibit the moisture approaching the corner region 216 (as well as the corner region 218) from actually entering and thus wetting the corner region 216. The moisture may not substantially move into contact with the first and/or second seam allowances 294, 297 and thus may not enter the corner regions 216 and/or 218. Thus, the first and second seam allowances 294, 297 are uniquely positioned generally away from the moisture regions of the reusable diaper 200 so as to help inhibit wicking of liquid into the corner regions 216, 218.

FIGS. 13-21 illustrate another exemplary embodiment of a reusable diaper (indicated generally at 300) embodying one or more aspects of the present disclosure. As shown in FIG. 13, there are interchangeable sets of corner tabs 317 of different sizes, which are releasably attachable to the reusable diaper 300 for adjusting and tailoring the diaper size to the wearer (e.g., one size fits all style, etc.), for example, to provide a relatively snug fit about the waist and leg openings of the wearer (e.g., infant, toddler, adult, etc.).

The corner tabs 317 include first and second opposite end portions 319 and 321 having spaced-apart female snap members 331, 333, respectively. These snap members 331, 331 may be snapped to corresponding male snap members 323, 325 respectively within forward and rearward pockets 303, 305 of the reusable diaper 300 as shown by FIGS. 15 through 17. In this example, the forward pockets 303 are closed end pockets disposed in the opposite lateral side portions of the forward waist portion 312, while the rearward pockets 305 are closed end pockets disposed in the opposite lateral side portions of the rearward waist portion 310. The reusable diaper 300 also includes a crotch portion 314 disposed generally between the first and second waist portions 310, 312. Other embodiments may include one or more pockets at other locations.

When releasably attached to the diaper 300, the corner tabs 317 define part of the waist of the diaper 300. Thus, selecting and releasably attaching a shorter corner tab 317 will reduce the functional waist as compared to the functional waist size when a longer tab 317 is used. Similarly, selecting and releasably attaching a shorter corner tab 317 will reduce the leg opening size as compared to the leg opening size when a longer tab 317 is used, as the corner tabs 317 include lower curved or contoured portions that defines part of the generally curved leg openings. Accordingly, the functional size of the waist and leg openings of the diaper 300 may be adjusted, changed, or tailored depending on which of length of corner tab 317 is selected and attached to the diaper 300.

With continued reference to FIGS. 15-17, FIG. 15 illustrates the reusable diaper 300 with the longest set of corner tabs 317 from FIG. 13 releasably attached to the reusable diaper 300 without any of the snap members 382, 384, 386 along the diaper's forward portion snapped together. By comparison, FIG. 16 illustrates the reusable diaper 300 with the intermediate length corner tabs 317 releasably attached to the reusable diaper 300 and with the top and middle rows of snap members 382, 384 along the diaper's forward portion snapped together, such that the diaper's functional waist size, leg opening size, and rise or crotch length is reduced when compared to FIG. 15. By way of further comparison, FIG. 17 illustrates the reusable diaper 300 with the shortest set of corner tabs 317 releasably attached to the reusable diaper 300 and with the top and bottom rows of snap members 382, 386 along the diaper's forward portion snapped together, such that the diaper's functional waist size, leg opening size, and rise or crotch length is even further reduced than what is shown in FIG. 16.

The size of the corner tabs 317 may be varied depending, for example, on whether the diaper is intended for use by an adult or toddler. In one example embodiment, first and second sets of interchangeable corner tabs are provided. In this example, each corner tab of the first set when unstretched may have an overall length of about 132 millimeters with a distance of about 99 millimeters separating the columns of snaps on the opposite end portions of the unstretched corner tab. But when the corner tabs of the first set are fully stretched each tab has an overall length of about 232 millimeters with a distance of about 200 millimeters separating the columns of snaps on the opposite end portions of the fully stretched corner tab. Also in this example, each corner tab of the second, shorter set when unstretched may have an overall length of about 80 millimeters with a distance of about 48 millimeters separating the columns of snaps on the opposite end portions of the unstretched corner tab. But when the corner tabs of the second set are fully stretched each tab has an overall length of about 135 millimeters with a distance of about 101 millimeters separating the columns of snaps on the opposite end portions of the fully stretched corner tab. Accordingly, interchanging the first and second sets of tabs provides about 304 millimeter maximum variance in the waist size of the diaper as determined by the total length separating the columns of snaps of the longer tabs when fully stretched (2×200 millimeters) and subtracting therefrom the total length separating the columns of snaps of the shorter tabs when unstretched (2×48 millimeters). The dimensions in this paragraph are provided herein for illustrative purposes only. The particular dimensions and values provided are not intended to limit the scope of the present disclosure. For example, other exemplary embodiments may include more or less than two sets of tabs (e.g., one set of tabs (e.g., FIG. 22, etc.), three sets of tabs (e.g., FIG. 13, etc.) and/or tabs having different configurations (e.g., longer, shorter, thicker, thinner, shaped differently, etc.).

The pockets 303, 305 are also configured to receive therein at least a portion of the corner tabs 317 when the forward and rearward waist portions 312, 310 are releasably attached by the corner tabs 317. The pockets 303, 305 are preferably configured to be substantially impervious to liquids, such that positioning of the end portions 319, 321 of the corner tabs 317 in the corresponding pockets 303, 305 helps inhibit wicking of liquid through the pockets 303, 305 and into the corner tabs 317. By keeping moisture from wicking to the corner tabs 317, the pockets 303, 305 help make changing the diaper 300 less disagreeable as the diaper changer will not have to handle moist corner tabs.

In this example, the snap members are plastic. Alternatively, the snap members can be formed from other materials, which are preferably relatively lightweight and durable to withstand repeated laundry cycles. Alternative embodiments may include corner tabs that include more or less snap members in other arrangements than what is shown in FIG. 13, such as that shown in FIG. 22. As another example, another embodiment may include male snap members on the corner tabs and female snap members within the pockets of the diaper. As a further example embodiment, the corner tabs and pockets may each have both male and female snap members. Still further embodiments may include a wide range of other suitable fastening means or fastening systems besides snaps, such as adhesives, buttons, clasps, Velcro® hook and loop closures, magnets, elastic straps, adjustable straps, combinations thereof, etc. Still yet further embodiments may include one of the end portions of a corner tab fixedly attached within a pocket and/or a corner tab that is foldable over itself to reduce the functional length of the corner tab.

The corner tabs 317 may be resiliently stretchable to permit some adjustability to the functional waist size of the reusable diaper as defined by the first and second waist portions 310, 312. In some embodiments, the corner tabs 317 may be formed from 95% polyester and 5% Lycra, which allows the corner tabs 317 to be stretchable and to maintain a flat profile when stretched or unstretched. Alternatively, the corner tab 317 may be formed using other suitable materials.

FIG. 18A illustrates the interior pockets 309, 311 of the diaper's outer shell or layer 358 in which the end portions 313, 315 of the liquid-absorbent pad 306 as shown by FIGS. 19-21. In FIGS. 18-20, the outermost portion or flaps 308 of the pockets 309, 311 are illustrated pulled back or opened so as to illustrate the exemplary manner by which the end portions 313, 315 of the liquid-absorbent pad 306 may be positioned within and releasable attached within the interior pockets 309, 311 of the outer shell 358.

As shown in FIG. 21, the end portions 313, 315 of the liquid-absorbent pad 306 within the interior pockets 309, 311 are substantially covered by the outermost portions or flaps 308 of the interior pockets 309, 311. This inhibits contact between those covered portions 313, 315 of the liquid-absorbent pad 306 and the diaper wearer or diaper changer. Also, in this example, the pockets' outermost portions or flaps 308 also substantially cover the Velcro®hook and loop closures 339, 341, 343, and 345 and thus inhibit contact between the skin or clothes of the diaper wearer and the Velcro® hook and loop closures. These flaps 308 may also help hold the liquid-absorbent pad 106 in place inside the diaper 300.

The outer shell 358 may be formed from a wide variety of materials. In this exemplary embodiment, the outer shell 358 is formed from polyester, such that the outer shell 358 is waterproof and substantially liquid-impervious to thereby resist wicking of moisture through the outer layer 358. Alternatively, the outer shell 358 may be formed from different materials.

The liquid-absorbent pad 306 may be formed from a wide variety of materials that are configured to absorb and store liquids therein. By way of example, the liquid-absorbent pad 306 may comprise one or more of microfibers, hemp, hydrocolloid materials, or any other suitable material configured to absorb and store liquids therein. In some exemplary embodiments, the liquid-absorbent pad 306 is formed from one or more of organic cotton material, microfiber terry, and/or suede cloth.

In this particular embodiment, the liquid-absorbent pad 306 is shown with Velcro® hook and loop closure strips 339, 341 on its outer or front side (FIG. 18B), Velcro® hook and loop closure strips 343, 345 on its inner or back side (FIG. 18C), and fold lines 347 and 349 (e.g., stitching, etc.). As shown by FIGS. 19-21, the Velcro® hook and loop closure strip 345 may be releasably attached to corresponding Velcro® hook and loop closure strip 351 within the pocket 311 of the diaper 300. In addition, any one of the other Velcro® hook and loop closures 339, 341, 345 may be selectively attached to the corresponding Velcro® hook and loop closure strip 353 within the pocket 309 of the diaper 300 as shown by FIGS. 19-21.

For example, in FIG. 19, the liquid-absorbent pad's strip 339 is attached to the strip 353 within the pocket 309 after the liquid-absorbent pad 306 has been partly folded over itself along the stitching or fold line 347. Folding the liquid-absorbent pad 306 along the fold line 347 reduces the functional length of the liquid-absorbent pad 306. In FIG. 20, the liquid-absorbent pad's strip 341 is attached to the strip 353 within the pocket 309 after the liquid-absorbent pad 306 has been partly folded over itself along the stitching or fold line 349, which creates a greater degree of overlap than that shown in FIG. 19. Accordingly, folding the liquid-absorbent pad 306 along the fold line 349 even further reduces the functional length of the liquid-absorbent pad 306. In FIG. 21, the liquid-absorbent pad 306 has not been folded and its strip 343 is attached to the strip 353 within the pocket 309. This lengthwise adjustability can allow the liquid-absorbent pad 306 to more precisely fit along the crotch 314 of the diaper 300, for example, when the functional rise or crotch length of the diaper is changed by way of the array of snaps along the forward portion of the diaper 300. Alternative embodiments may include a liquid-absorbent pad having more or less strips of hook and loop closures in other arrangements to accommodate lengthwise adjustability to the liquid-absorbent pad. Further embodiments may include a liquid-absorbent pad having a wide range of other suitable fastening means or fastening systems besides Velcro® hook and loop closures, such as adhesives, buttons, clasps, snaps, magnets, elastic straps, adjustable straps, combinations thereof, etc. Still further embodiments may include a liquid-absorbent pad without any such lengthwise adjustability.

Accordingly, the reusable diaper 300 may be put on a wearer with the liquid-absorbent pad 306 positioned against the skin of the wearer. In which case, the liquid-absorbent pad 306 can absorb moisture (e.g., bodily discharge, urine, sweat, etc.). When the liquid-absorbent pad 306 has become saturated, the liquid-absorbent pad 306 may be removed and then washed or laundered along with or separately from the diaper 300. After the diaper 300 and liquid-absorbent pad 306 have been satisfactorily washed and dried, the liquid-absorbent pad 306 may be reattached to the diaper 300 with an adjusted length as described above so as to more precisely fit along the crotch 314 of the diaper 300. At which point, the diaper 300 may be reused.

The snap members 382, 384, 386 of diaper 300 may be substantially the same as or similar to the snap members 182, 184, 186 of reusable diaper 100 described above. As before with diaper 100, the diaper 300 is illustrated with a three-by-three array of snap members such that the snap members are horizontally arranged and aligned in the three rows and vertically arranged and aligned in the three columns. Advantageously, having at least three columns may provide a more snug and precise fit to the diaper wearer, for example, by reducing the extent to which the crotch portion hangs down below the wearer. The three-by-three arrangement can eliminate or at least reduce the bulge in the middle front of the diaper that typically occurs when there are only two columns of snaps due to the fabric bulging out between the two snaps. The three-by-three snap arrangement may enable the diaper to be more of a one-size fits all cloth diaper.

In alternative embodiments, the reusable diaper 300 may include more or less snap options and/or snap members in other arrangements than what is shown in FIGS. 13-21. For example, another embodiment may include two rows of male snap members with only one row of female snap members. As another example embodiment, a diaper may include a row having both male and female snap members. Additional examples include diapers having more or less than three rows of snap members and/or more or less than three columns of snap members. Still further embodiments may include a wide range of other suitable fastening means or fastening systems besides snaps, such as adhesives, buttons, clasps, Velcro® hook and loop closures, magnets, elastic straps, adjustable straps, combinations thereof, etc.

In some embodiments, the reusable diaper 300 and interchangeable tabs 317 may be provided in a package or as a kit. In such embodiments, the package may include indicia (e.g., graphic illustrations, instructions, etc.) explaining how the size of the reusable diaper 300 may be adjusted by interchanging the tabs. In yet other embodiments, the tabs 317 may be provided separately from the reusable diaper 300.

FIG. 22 illustrate another exemplary embodiment of a corner tab 417 embodying one or more aspects of the present disclosure. As shown in FIG. 22, the corner tab 417 includes first and second opposite end portions 419 and 421. The first end portion 419 includes two columns of spaced-apart female snap members 431. The second end portion 421 includes three columns of spaced-apart female snap members 433. These columns of female snap members 431 and 433 provide the corner tab 417 with different snap options, such that corner tab 417 may be releasably attached to a reusable diaper 400 (FIGS. 23 and 24) at different functional lengths depending on which of the columns of snaps are used.

For example, FIG. 23 illustrates the reusable diaper 400 having the corner tab shown in FIG. 22. In this example, the corner tab 417 is releasably attached via the outermost columns of snap members, which are snapped to corresponding male snap members 423, 425 respectively within forward and rearward pockets 403, 405 of the reusable diaper 400. This provides the corner tab 416 with the longest of the functional length options provide by the columns of snap members 431, 433.

By way of comparison, FIG. 24 illustrates the reusable diaper 400 with the corner tab 417 releasably attached via the corner tab's innermost columns of snap members. In this example then, the corner tab 417 has the shortest of the functional length options. This, in turn, also reduces the diaper's functional waist size and leg opening size as compared to FIG. 23.

As shown in FIGS. 23 and 24, the corner tab 417 includes a lower curved portion that defines part of the generally curved leg opening, such that reducing the functional length of the corner tab 417 also reduces the leg opening size. Also shown in FIG. 24, the top and bottom rows of snap members along the diaper's forward portion have been snapped together, which thereby further reduces the diaper's functional waist size, leg opening size, and rise or crotch length as compared to that shown in FIG. 23. Accordingly, the corner tab 417 thus allows for adjustment and tailoring of the diaper size to the wearer, for example, to provide a relatively snug fit about the waist and leg openings of the wearer (e.g., infant, toddler, adult, etc.).

In addition to what is shown in FIGS. 23 and 24, the corner tab 417 may be releasable attached to the diaper 400 using other combinations of the columns of snap members 431, 433. In this exemplary way, the waist size and leg opening size of the diaper 400 may thus be adjusted without having to completely remove and interchange corner tabs.

The pockets 403, 405 of the reusable diaper 400 may be substantially the same as or similar to the pockets 303, 305 of reusable diaper 300 described above. For example, the pockets 404, 405 may also be configured to be substantially impervious to liquids, such that positioning of the end portions 419, 421 of the corner tabs 417 therein helps inhibit wicking of liquid through the pockets 403, 405 and into the corner tabs 417. The pockets 403, 405 may be configured to be deeper with a sufficient depth so as to allow the end portions 419, 421 of the corner tab 417 to be inserted farther into the respective pockets 403, 405 to thereby allow the innermost columns of snap members to be inserted into the pockets 403, 405 for being snapped into the snap members 423, 425 within the pockets 403, 405.

In addition to, or as an alternative to, the corner tabs providing different attachment options, the pockets may instead or additionally include different attachment options. For example, the pockets 403, 405 may include more than one column of snap members to thereby allow the functional length of the corner tab 417 to be changed depending on which column of snap members within the pockets 403, 405 is used to attach the corner tab 417.

In this illustrated embodiment of FIGS. 22-24, the snap members are plastic in this example. Alternatively, the snap members can be formed from other materials, which are preferably relatively lightweight and durable to withstand repeated laundry cycles.

The corner tab's first end portion 419 includes two columns of three spaced-apart female snap members 431, while the second end portion 421 includes two columns of four spaced-apart female snap members 433. Alternative embodiments may include corner tabs that include more or less snap options and/or snap members in other arrangements than what is shown in FIG. 22. For example, another embodiment may include male snap members on the corner tab and the female snap members within the pockets of the diaper. As another example embodiment, the corner tab and pockets may each have both male and female snap members. Additional examples include corner tabs with more or less columns and/or rows of snap members than that shown in FIG. 22. Still further embodiments may include a wide range of other suitable fastening means or fastening systems besides snaps, such as adhesives, buttons, clasps, Velcro® hook and loop closures, magnets, elastic straps, adjustable straps, combinations thereof, etc. Still yet further embodiments may include one of the end portions of the corner tab fixedly attached within a pocket and/or a corner tab that is foldable over itself to reduce the functional length of the corner tab.

The corner tab 417 may be resiliently stretchable to permit some adjustability to the functional waist size of the reusable diaper as defined by the first and second waist portions. In some embodiments, the corner tab 417 may be formed from 95% polyester and 5% Lycra, which allows the corner tab 417 to be stretchable and to maintain a flat profile when stretched or unstretched. Alternatively, the corner tab 417 may be formed using other suitable materials.

Other aspects of the present disclosure relate to methods, such as methods of using any one or more of the various reusable diapers (e.g., 100, 200, 300, 400, etc.) disclosed herein. In an exemplary embodiment, a method generally includes removing at least one corner tab from a diaper and attaching at least one different corner tab that is longer or shorter than the removed corner tab. In another exemplary embodiment, a method generally includes selecting at least one corner tab from a plurality of differently sized corner tabs, and attaching the selected corner tab to a diaper. In a further exemplary embodiment, a method generally includes changing a size of a diaper by detaching at least one end portion of a corner tab and reattaching the end portion of the corner tab to the diaper such that the functional length of the corner tab is different. Accordingly, these exemplary method embodiments thus allow the size of the diaper to be changed or tailored to the intended diaper wearer (e.g., infant, toddler, adult, etc.).

In another exemplary embodiment, a method generally includes positioning at least one liquid-absorbent insert through at least one slit or opening into at least one pocket of a reusable diaper. The method may further include closing at least one flap to substantially cover the at least one slit or opening, whereby the at least one flap inhibits contact between the diaper wearer and the at least one liquid-absorbent insert and/or inhibits the inadvertent removal of the at least one liquid-absorbent insert from the at least one pocket.

In some embodiments, the method may include opening the at least one flap to thereby expose the at least one slit or opening and allow access to the at least one pocket. The method may include removing at least one liquid-absorbent insert from the at least one pocket out through the at least one slit or opening. After laundering or washing the diaper, at least one replacement liquid-absorbent insert may be positioned through the at least one slit into the at least one pocket. As another example, a method may include removing the reusable diaper from a wearer before opening the at least one flap, removing the at least one liquid-absorbent insert, washing or laundering the diaper and the liquid-absorbent insert, and positioning the liquid-absorbent insert within the pocket.

In some embodiments, a method may further comprise selectively adjusting a functional waist size of the reusable diaper to a wearer, by stretching corner regions of a first waist portion of the reusable diaper, and then releasably attaching tabs associated with the corner regions to a second waist portion of the reusable diaper. In some preferred embodiments, the tabs may be releasably attached to the second waist portion by using hook-and-loop fasteners. Additional embodiments, however, may alternatively comprise snaps, buttons, adhesives, magnets, combinations thereof, etc.

Numerical dimensions and values are provided herein for illustrative purposes only. The particular dimensions and values provided are not intended to limit the scope of the present disclosure.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter. The disclosure of a first value and a second value for a given parameter can be interpreted as disclosing that any value between the first and second values could also be employed for the given parameter. Similarly, it is envisioned that disclosure of two or more ranges of values for a parameter (whether such ranges are nested, overlapping or distinct) subsume all possible combination of ranges for the value that might be claimed using endpoints of the disclosed ranges.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A reusable diaper comprising:
   a forward waist portion;
   a rearward waist portion;
   at least one corner tab releasably attachable to the forward and rearward waist portions, such that the corner tab is detachable and completely separable from the diaper; and
   at least one pocket substantially impervious to liquids, and configured to receive therein at least a portion of the corner tab when the forward and rearward waist portions are releasably attached by the corner tab;
   whereby the positioning of the portion of the corner tab in the pocket helps inhibit wicking of liquid through the pocket and into the corner tab.

2. The reusable diaper of claim 1, wherein:
   the at least one pocket includes a first pocket disposed in a first lateral side portion of the forward waist portion, and a second pocket disposed in a first lateral side portion of the rearward waist portion; and
   the at least one corner tab includes a first corner tab having first and second opposite end portions releasably attachable to the respective forward and rearward waist portions within the respective first and second pockets.

3. The reusable diaper of claim 2, wherein:
   the at least one pocket further includes a third pocket disposed in a second lateral side portion of the forward waist portion, and a fourth pocket disposed in a second lateral side portion of the rearward waist portion; and
   the at least one corner tab further includes a second corner tab having first and second opposite end portions releasably attachable to the respective forward and rearward waist portions within the respective third and fourth pockets.

4. The reusable diaper of claim 1, wherein:
   the at least one pocket includes first, second, third, and fourth pockets; and
   the at least one corner tab includes:
      a first corner tab having opposite end portions releasably attachable in the respective first and second pockets; and
      a second corner tab having opposite end portions releasably attachable in the respective third and fourth pockets.

5. The reusable diaper of claim 1, wherein the at least one corner tab is resiliently stretchable and/or foldable over itself to thereby permit adjustability to a functional waist size of the reusable diaper as defined by the forward and rearward waist portions when releasably attached by the corner tab.

6. The reusable diaper of claim 1, wherein:
   the at least one corner tab includes at least one fastener;
   the at least one pocket includes at least one fastener therein such that the corner tab's fastener is releasably attachable to the fastener within the pocket.

7. The reusable diaper of claim 6, wherein the fasteners comprise one or more rows and/or columns of spaced apart snaps on the corner tab and/or within the pocket, whereby the snaps permit adjustability to a functional waist size of the reusable diaper as defined by the forward and rearward waist portions when releasably attached by the corner tab.

8. The reusable diaper of claim 6, wherein the at least one corner tab includes a plurality of fasteners spaced apart along a length of at least one end portion of the corner tab, and the at least one pocket is configured to receive the end portion of the corner tab therein, thereby providing a plurality of attachment options that allow a user to adjust a functional length of the corner tab and thereby change a size of the diaper without having to completely remove the corner tab from the diaper.

9. The reusable diaper of claim 1, further comprising:
   an outer shell configured to be substantially liquid-impervious and defining first and second interior pockets along the respective forward and rearward waist portions; and
   a liquid-absorbent pad having first and second opposite end portions releasably attachable to the outer shell within the first and second interior pockets, such that the liquid-absorbent pad is detachable and completely separable from the diaper.

10. The reusable diaper of claim 1, wherein the corner tab is formed of resiliently stretchable material comprising polyester and LYCRA spandex, which material permits the corner tab to maintain a flat profile when stretched or unstretched.

11. The reusable diaper of claim 1:
    wherein the at least one pocket includes:
       a first closed end pocket disposed in a first lateral side portion of the forward waist portion;
       a second closed end pocket disposed in a first lateral side portion of the rearward waist portion;
       a third closed end pocket disposed in a second lateral side portion of the forward waist portion; and
       a fourth closed end pocket disposed in a second lateral side portion of the rearward waist portion;
    wherein the at least one corner tab includes:
       a first corner tab having first and second opposite end portions having fasteners releasably attachable to fasteners within the respective first and second pockets; and
       a second corner tab having first and second opposite end portions having fasteners releasably attachable to fasteners within the respective third and fourth pockets;
    wherein the first and second corner tab define part of a generally curved right and left leg openings, respectively of the diaper when releasably attached to the forward and rearward waist portions.

12. The reusable diaper of claim 11, wherein the at least one corner tab further comprises:
    a third corner tab having first and second opposite end portions having fasteners releasably attachable to fasteners within the respective first and second pockets, such that the third corner tab is interchangeable with the first corner tab; and
    a fourth corner tab having first and second opposite end portions having fasteners releasably attachable to fasteners within the respective third and fourth pockets, such that the fourth corner tab is interchangeable with the second corner tab;
    wherein the third and fourth corner tabs are sized differently than the first and second corner tabs to thereby permit adjustability to a size of the right and left leg openings and/or a functional waist size of the reusable diaper as defined by the forward and rearward waist portions.

13. A reusable diaper comprising:
    a forward waist portion;
    a rearward waist portion;
    first and second sets of corner tabs releasably attachable to the forward and rearward waist portions, such that the second set of corner tabs is interchangeable with the first set of corner tabs, the second set of corner tabs sized differently than the first set of corner tabs such that:
       the diaper has a first size when the forward and rearward waist portions are releasably attached by the first set of corner tabs; and the diaper has a second size different than the first size when the forward and rearward waist portions are releasably attached by the second set of corner tabs.

14. The reusable diaper of claim 13, wherein the corner tabs define portions of the waist and leg openings of the diaper when releasably attached to the forward and rearward waist portions, such that the interchanging the first and second sets of corner tabs changes the size of the waist and leg openings of the diaper.

15. The reusable diaper of claim 13, wherein the diaper includes more than two sets of corner tabs having different sizes.

16. The reusable diaper of claim 13, further comprising pockets, and wherein the corner tabs have end portions releasably attachable to the forward and rearward waist portions within the pockets.

17. The reusable diaper of claim 16, wherein the corner tabs include fasteners and the pockets include fasteners therein, such that the fasteners of the corner tabs are releasably attachable to corresponding fasteners in the pockets.

18. The reusable diaper of claim 16, wherein the fasteners comprises one or more rows and/or columns of spaced apart snaps to thereby permit adjustability to the size of the diaper.

19. The reusable diaper of claim 16, wherein at least one of the corner tabs includes a plurality of fasteners spaced apart along a length of at least one end portion of the corner tab, and at least one of the pockets is configured to receive the end portion having the plurality of fasteners, thereby providing a plurality of attachment options that allow a user to adjust a functional length of the corner tab and thereby change a size of the diaper without having to completely remove the corner tab from the diaper.

20. The reusable diaper of claim 13, wherein the corner tabs are formed of resiliently stretchable material comprising polyester and LYCRA spandex, which material permits the corner tabs to maintain a flat profile when stretched or unstretched.

21. The reusable diaper of claim 13, further comprising:
an outer shell configured to be substantially liquid-impervious and defining first and second interior pockets along the respective forward and rearward waist portions; and
a liquid-absorbent pad having first and second opposite end portions releasably attachable to the outer shell within the first and second interior pockets, such that the liquid-absorbent pad is detachable and completely separable from the diaper.

22. A reusable diaper comprising:
a forward waist portion;
a first pocket disposed in a lateral side portion of the forward waist portion; and a second pocket disposed in an opposite lateral side portion of the forward waist portion;
a rearward waist portion;
a third pocket disposed in a lateral side portion of the rearward waist portion and a fourth pocket disposed in an opposite lateral side portion of the rearward waist portion;
first and second pairs of corner tabs each having front and back end portions releasably attachable to the respective forward and rearward waist portions within the respective first, second, third, and fourth pockets, such that the second pair of corner tabs is interchangeable with the first pair of corner tabs, the second pair of corner tabs sized differently than the first pair of corner tabs;
wherein the corner tabs define portions of the waist and leg openings of the diaper when releasably attached to the forward and rearward waist portions, such that interchanging the first and second pairs of corner tabs changes the size of the waist and leg openings of the diaper.

* * * * *